(12) United States Patent
Blackwell et al.

(10) Patent No.: US 11,760,801 B2
(45) Date of Patent: Sep. 19, 2023

(54) ANTI-CEACAM ANTIBODIES AND USES THEREOF

(71) Applicant: Janssen Biotech, Inc., Horsham, PA (US)

(72) Inventors: Wendell Lamar B Blackwell, Philadelphia, PA (US); Douglas V. Dolfi, Norristown, PA (US); Cassandra L. Lowenstein, Ambler, PA (US); Raluca I. Verona, Swarthmore, PA (US)

(73) Assignee: Janssen Biotech, Inc., Horsham, PA (US)

( * ) Notice: Subject to any disclaimer, the term of this patent is extended or adjusted under 35 U.S.C. 154(b) by 34 days.

(21) Appl. No.: 17/019,747

(22) Filed: Sep. 14, 2020

(65) Prior Publication Data

US 2021/0095024 A1   Apr. 1, 2021

Related U.S. Application Data

(60) Provisional application No. 62/907,224, filed on Sep. 27, 2019.

(51) Int. Cl.
| | | |
|---|---|---|
| C07K 16/28 | (2006.01) | |
| A61P 35/00 | (2006.01) | |
| A61K 39/395 | (2006.01) | |
| A61K 45/06 | (2006.01) | |
| A61K 39/00 | (2006.01) | |
| C07K 16/30 | (2006.01) | |

(52) U.S. Cl.
CPC .... *C07K 16/2803* (2013.01); *A61K 39/39541* (2013.01); *A61K 39/39558* (2013.01); *A61K 45/06* (2013.01); *A61P 35/00* (2018.01); *C07K 16/3007* (2013.01); *A61K 2039/505* (2013.01); *C07K 2317/24* (2013.01); *C07K 2317/31* (2013.01); *C07K 2317/74* (2013.01); *C07K 2317/92* (2013.01)

(58) Field of Classification Search
CPC ............ C07K 16/2803; C07K 16/3007; C07K 2317/24; C07K 2317/31; C07K 2317/74; C07K 2317/92; A61P 35/00; A61K 39/39558; A61K 45/06; A61K 2039/505
See application file for complete search history.

(56) References Cited

U.S. PATENT DOCUMENTS

| | | |
|---|---|---|
| 4,816,567 A | 3/1989 | Cabilly et al. |
| 5,225,539 A | 7/1993 | Winter |
| 5,500,362 A | 3/1996 | Robinson et al. |
| 5,648,237 A | 7/1997 | Carter |
| 5,693,761 A | 12/1997 | Queen et al. |
| 5,693,762 A | 12/1997 | Queen et al. |
| 5,750,373 A | 5/1998 | Garrard et al. |
| 5,770,429 A | 6/1998 | Lonberg et al. |
| 5,789,199 A | 8/1998 | Joly et al. |
| 5,821,337 A | 10/1998 | Carter et al. |
| 5,840,523 A | 11/1998 | Simmons et al. |
| 5,959,177 A | 9/1999 | Hein et al. |
| 6,040,498 A | 3/2000 | Stomp et al. |
| 6,075,181 A | 6/2000 | Kucherlapati et al. |
| 6,150,584 A | 11/2000 | Kucherlapati et al. |
| 6,194,551 B1 | 2/2001 | Idusogie et al. |
| 6,251,856 B1 | 6/2001 | Markussen et al. |
| 6,417,429 B1 | 7/2002 | Hein et al. |
| 6,420,548 B1 | 7/2002 | Vezina et al. |
| 6,737,056 B1 | 5/2004 | Presta |
| 6,982,321 B2 | 1/2006 | Winter |
| 7,041,870 B2 | 5/2006 | Tomizuka et al. |
| 7,087,409 B2 | 8/2006 | Barbas, III et al. |
| 7,125,978 B1 | 10/2006 | Vezina et al. |
| 7,189,826 B2 | 3/2007 | Rodman |
| 7,332,581 B2 | 2/2008 | Presta |
| 7,371,826 B2 | 5/2008 | Presta |
| 7,521,541 B2 | 4/2009 | Eigenbrot et al. |
| 7,527,791 B2 | 5/2009 | Adams et al. |
| 2005/0014934 A1 | 1/2005 | Hinton et al. |
| 2005/0079574 A1 | 4/2005 | Bond |
| 2005/0119455 A1 | 6/2005 | Fuh et al. |
| 2005/0266000 A1 | 12/2005 | Bond et al. |
| 2007/0061900 A1 | 3/2007 | Murphy et al. |
| 2007/0117126 A1 | 5/2007 | Sidhu et al. |
| 2007/0160598 A1 | 7/2007 | Dennis et al. |
| 2007/0237764 A1 | 10/2007 | Birtalan et al. |
| 2007/0292936 A1 | 12/2007 | Barthelemy et al. |
| 2009/0002360 A1 | 1/2009 | Chen et al. |
| 2011/0064653 A1 | 3/2011 | Hansen et al. |

FOREIGN PATENT DOCUMENTS

| | | |
|---|---|---|
| WO | WO 1986/01533 A1 | 3/1986 |
| WO | WO 1988/01649 A1 | 3/1988 |
| WO | WO 1990/07861 A1 | 7/1990 |
| WO | WO 1992/01047 A1 | 1/1992 |
| WO | WO 1994/13804 A1 | 6/1994 |
| WO | WO 1997/02671 A2 | 1/1997 |

(Continued)

OTHER PUBLICATIONS

Wu et al. (1970) *J Exp Med* 132: 211-50.

(Continued)

*Primary Examiner* — Mark Halvorson
*Assistant Examiner* — Dennis J Sullivan

(57) ABSTRACT

The disclosure provided herein relates to monospecific and multispecific antibodies, that bind CEACAM1 and optionally CEACAM5 and/or CEACAM6, and methods of producing and using the described antibodies.

23 Claims, 14 Drawing Sheets

Specification includes a Sequence Listing.

(56) References Cited

FOREIGN PATENT DOCUMENTS

| WO | WO 1998/44001 A1 | 10/1998 |
| WO | WO 1999/51642 A1 | 10/1999 |
| WO | WO 2000/55119 A1 | 9/2000 |
| WO | WO 2004/056312 A2 | 7/2004 |
| WO | WO 2005/100402 A1 | 10/2005 |
| WO | WO 2006/029879 A2 | 3/2006 |
| WO | WO 2009/085462 A1 | 7/2009 |
| WO | WO 2010/125571 A1 | 11/2010 |
| WO | WO 2013/082366 A1 | 6/2013 |
| WO | WO 2014/022332 A1 | 2/2014 |
| WO | WO 2014/093908 A2 | 6/2014 |
| WO | WO 2015/166484 A1 | 11/2015 |

OTHER PUBLICATIONS

Chothia et al. (1987) *J Mol Biol* 196: 901-17.
Lefranc et al. (2003) *Dev Comp Immunol* 27: 55-77.
Martin and Thornton (1996) *J Bmol Biol* 263: 800-15.
Honegger and Pluckthun, (2001) *J Mol Biol* 309:657-70.
Almagro, *Mol Recognit* 17:132-43, 2004.
Knappik et al., (2000) J Mol Biol 296:57-86.
Shi et al., (2010) J Mol Biol 397:385-96.
Morrison et al., *Proc. Natl. Acad. Sci. USA*, 81:6851-6855 (1984).
Almagro and Fransson, *Front. Biosci.* 13:1619-1633 (2008).
Riechmann et al., *Nature* 332:323-329 (1988).
Queen et al., *Proc. Nat'l Acad. Sci. USA* 86:10029-10033 (1989).
Kashmiri et al., *Methods* 36:25-34 (2005).
Padlan, *Mol. Immunol.* 28:489-498 (1991).
Dall'Acqua et al., *Methods* 36:43-60 (2005).
Osbourn et al., *Methods* 36:61-68 (2005).
Klimka et al., *Br. J. Cancer,* 83:252-260 (2000).
Sims et al. *J. Immunol.* 151:2296 (1993).
Carter et al. *Proc. Natl. Acad. Sci. USA,* 89:4285 (1992).
Presta et al. *J. Immunol.*, 151:2623 (1993).
Baca et al., *J. Biol. Chem.* 272:10678-10684 (1997).
Rosok et al., *J. Biol. Chem.* 271:22611-22618 (1996).
Van Dijk and van de Winkel, *Curr. Opin. Pharmacol.* 5: 368-74 (2001).
Lonberg, *Curr. Opin. Immunol.* 20:450-459 (2008).
Lonberg, *Nat. Biotech.* 23:1117-1125 (2005).
Kozbor J., "A human hybrid myeloma for production of human monoclonal antibodies," *Immunol.*, 133: 3001 (1984).
Boemer et al., "Production of antigen-specific human monoclonal antibodies from in vitro-primed human splenocytes," *J. Immunol.*, 147: 86 (1991).
Li et al., *Proc. Natl. Acad. Sci. USA*, 103:3557-3562 (2006).
Vollmers and Brandlein, *Histology and Histopathology*, 20(3):927-937 (2005).
Vollmers and Brandlein, *Methods and Findings in Experimental and Clinical Pharmacology*, 27(3):185-91 (2005).
Hoogenboom et al. in *Methods in Molecular Biology* 178:1-37 (O'Brien et al., ed., Human Press, Totowa, N.J., 2001).
McCafferty et al., *Nature* 348:552-554.
Clackson et al., *Nature* 352: 624-628 (1991).
Marks et al., *J. Mol. Biol.* 222: 581-597 (1992).
Marks and Bradbury, in *Methods in Molecular Biology* 248:161-175 (Lo, ed., Human Press, Totowa, N.J., 2003).
Sidhu et al., *J. Mol. Biol.* 338(2): 299-310 (2004).
Lee et al., *J. Mol. Biol.* 340(5): 1073-1093 (2004).
Fellouse, *Proc. Natl. Acad. Sci. USA* 101(34): 12467-12472 (2004).
Lee et al., *J. Immunol. Methods* 284(1-2): 119-132 (2004).
Winter et al., *Ann. Rev. Immunol.,* 12: 433-455 (1994).
Griffiths et al., *EMBO J,* 12: 725-734 (1993).
Hoogenboom and Winter, *J. Mol. Biol.*, 227: 381-388 (1992).
Ravetch and Kinet, *Annu, Rev. Immunol.* 9:457-492 (1991).
Hellstrom, I. et al. *Proc. Nat'l Acad. Sci. USA* 83:7059-7063 (1986).
Hellstrom, I et al., *Proc. Nat'l Acad. Sci. USA* 82:1499-1502 (1985).
Bruggemann, M. et al., *J. Exp. Med.* 166:1351-1361 (1987).
Clynes et al. *Proc. Nat'l Acad. Sci. USA* 95:652-656 (1998).
Gazzano-Santoro et al., *J. Immunol. Methods* 202:163 (1996).
Cragg, M. S. et al., *Blood* 101:1045-1052 (2003).
Cragg, M. S, and M. J. Glennie, *Blood* 103:2738-2743 (2004).
Petkova, S. B. et al., *Int'l. Immunol.* 18(12):1759-1769 (2006).
Shields et al., *J. Biol. Chem.* 9(2): 6591-6604 (2001).
Idusogie et al. *J. Immunol.* 164: 4178-4184 (2000).
Guyer et al., *J. Immunol.* 117:587 (1976).
Kim et al., *J. Immunol.* 24:249 (1994).
Gerngross, *Nat. Biotech.* 22:1409-1414 (2004).
Li et al., *Nat. Biotech.* 24:210-215 (2006).
Graham et al., *J. Gen Virol.* 36:59 (1977).
Mather, *Biol. Reprod.* 23:243-251 (1980).
Mather et al., *Annals N.Y. Acad. Sci.* 383:44-68 (1982).
Urlaub et al., *Proc. Natl. Acad. Sci. USA* 77:4216 (1980).
Goodson, R. J. & Katre, N. V. (1990) *Bio/Technology* 8, 343.
Kogan, T. P. (1992) *Synthetic Comm.* 22, 2417.
Osborn, et al. (2013) J Immunol 190(4): 1481-1490.
International Search Authority, Written Opinion, PCT Appl. No. PCT/IB2020/058523, dated Dec. 7, 2020.
Blumenthal, "Inhibition of Adhesion, Invasion, and Metastasis by Antibodies Targeting CEACAM6 (NCA-90) and CEACAM5 (Carcinoembryonic Antigen)", Cancer Research, vol. 65, No. 19, Oct. 1, 2005, pp. 8809-8817.

SEQUENCE LISTING

```
<160> NUMBER OF SEQ ID NOS: 102

<210> SEQ ID NO 1
<211> LENGTH: 526
<212> TYPE: PRT
<213> ORGANISM: Homo sapiens

<400> SEQUENCE: 1

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
                20                  25                  30

Thr Ala Gln Leu Thr Thr Glu Ser Met Pro Phe Asn Val Ala Glu Gly
            35                  40                  45

Lys Glu Val Leu Leu Leu Val His Asn Leu Pro Gln Gln Leu Phe Gly
        50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
                100                 105                 110

Thr Gln Asn Asp Thr Gly Phe Tyr Thr Leu Gln Val Ile Lys Ser Asp
            115                 120                 125

Leu Val Asn Glu Glu Ala Thr Gly Gln Phe His Val Tyr Pro Glu Leu
130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335
```

```
Val Thr Gly Asp Lys Asp Ser Val Asn Leu Thr Cys Ser Thr Asn Asp
            340                 345                 350

Thr Gly Ile Ser Ile Arg Trp Phe Lys Asn Gln Ser Leu Pro Ser
            355                 360                 365

Ser Glu Arg Met Lys Leu Ser Gln Gly Asn Thr Thr Leu Ser Ile Asn
    370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
                405                 410                 415

Asn Ala Leu Pro Gln Glu Asn Gly Leu Ser Pro Gly Ala Ile Ala Gly
            420                 425                 430

Ile Val Ile Gly Val Val Ala Leu Val Ala Leu Ile Ala Val Ala Leu
            435                 440                 445

Ala Cys Phe Leu His Phe Gly Lys Thr Gly Arg Ala Ser Asp Gln Arg
    450                 455                 460

Asp Leu Thr Glu His Lys Pro Ser Val Ser Asn His Thr Gln Asp His
465                 470                 475                 480

Ser Asn Asp Pro Pro Asn Lys Met Asn Glu Val Thr Tyr Ser Thr Leu
                485                 490                 495

Asn Phe Glu Ala Gln Gln Pro Thr Gln Pro Thr Ser Ala Ser Pro Ser
            500                 505                 510

Leu Thr Ala Thr Glu Ile Ile Tyr Ser Glu Val Lys Lys Gln
            515                 520                 525

<210> SEQ ID NO 2
<211> LENGTH: 394
<212> TYPE: PRT
<213> ORGANISM: Homo sapiens

<400> SEQUENCE: 2

Gln Leu Thr Thr Glu Ser Met Pro Phe Asn Val Ala Glu Gly Lys Glu
1               5                   10                  15

Val Leu Leu Leu Val His Asn Leu Pro Gln Gln Leu Phe Gly Tyr Ser
            20                  25                  30

Trp Tyr Lys Gly Glu Arg Val Asp Gly Asn Arg Gln Ile Val Gly Tyr
            35                  40                  45

Ala Ile Gly Thr Gln Gln Ala Thr Pro Gly Pro Ala Asn Ser Gly Arg
    50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                85                  90                  95

Asn Glu Glu Ala Thr Gly Gln Phe His Val Tyr Pro Glu Leu Pro Lys
            100                 105                 110

Pro Ser Ile Ser Ser Asn Asn Ser Asn Pro Val Glu Asp Lys Asp Ala
            115                 120                 125

Val Ala Phe Thr Cys Glu Pro Glu Thr Gln Asp Thr Thr Tyr Leu Trp
    130                 135                 140

Trp Ile Asn Asn Gln Ser Leu Pro Val Ser Pro Arg Leu Gln Leu Ser
145                 150                 155                 160

Asn Gly Asn Arg Thr Leu Thr Leu Leu Ser Val Thr Arg Asn Asp Thr
                165                 170                 175

Gly Pro Tyr Glu Cys Glu Ile Gln Asn Pro Val Ser Ala Asn Arg Ser
```

```
                180             185             190
Asp Pro Val Thr Leu Asn Val Thr Tyr Gly Pro Asp Thr Pro Thr Ile
            195                 200                 205

Ser Pro Ser Asp Thr Tyr Tyr Arg Pro Gly Ala Asn Leu Ser Leu Ser
210                 215                 220

Cys Tyr Ala Ala Ser Asn Pro Pro Ala Gln Tyr Ser Trp Leu Ile Asn
225                 230                 235                 240

Gly Thr Phe Gln Gln Ser Thr Gln Glu Leu Phe Ile Pro Asn Ile Thr
            245                 250                 255

Val Asn Asn Ser Gly Ser Tyr Thr Cys His Ala Asn Asn Ser Val Thr
        260                 265                 270

Gly Cys Asn Arg Thr Thr Val Lys Thr Ile Ile Val Thr Glu Leu Ser
        275                 280                 285

Pro Val Val Ala Lys Pro Gln Ile Lys Ala Ser Lys Thr Thr Val Thr
    290                 295                 300

Gly Asp Lys Asp Ser Val Asn Leu Thr Cys Ser Thr Asn Asp Thr Gly
305                 310                 315                 320

Ile Ser Ile Arg Trp Phe Phe Lys Asn Gln Ser Leu Pro Ser Ser Glu
            325                 330                 335

Arg Met Lys Leu Ser Gln Gly Asn Thr Thr Leu Ser Ile Asn Pro Val
            340                 345                 350

Lys Arg Glu Asp Ala Gly Thr Tyr Trp Cys Glu Val Phe Asn Pro Ile
        355                 360                 365

Ser Lys Asn Gln Ser Asp Pro Ile Met Leu Asn Val Asn Tyr Asn Ala
        370                 375                 380

Leu Pro Gln Glu Asn Gly Leu Ser Pro Gly
385                 390

<210> SEQ ID NO 3
<211> LENGTH: 702
<212> TYPE: PRT
<213> ORGANISM: Homo sapiens

<400> SEQUENCE: 3

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160
```

-continued

```
Asp Ala Val Ala Phe Thr Cys Glu Pro Glu Thr Gln Asp Ala Thr Tyr
                165                 170                 175
Leu Trp Trp Val Asn Asn Gln Ser Leu Pro Val Ser Pro Arg Leu Gln
            180                 185                 190
Leu Ser Asn Gly Asn Arg Thr Leu Thr Leu Phe Asn Val Thr Arg Asn
        195                 200                 205
Asp Thr Ala Ser Tyr Lys Cys Glu Thr Gln Asn Pro Val Ser Ala Arg
    210                 215                 220
Arg Ser Asp Ser Val Ile Leu Asn Val Leu Tyr Gly Pro Asp Ala Pro
225                 230                 235                 240
Thr Ile Ser Pro Leu Asn Thr Ser Tyr Arg Ser Gly Glu Asn Leu Asn
                245                 250                 255
Leu Ser Cys His Ala Ala Ser Asn Pro Pro Ala Gln Tyr Ser Trp Phe
            260                 265                 270
Val Asn Gly Thr Phe Gln Gln Ser Thr Gln Glu Leu Phe Ile Pro Asn
        275                 280                 285
Ile Thr Val Asn Asn Ser Gly Ser Tyr Thr Cys Gln Ala His Asn Ser
    290                 295                 300
Asp Thr Gly Leu Asn Arg Thr Thr Val Thr Thr Ile Thr Val Tyr Ala
305                 310                 315                 320
Glu Pro Pro Lys Pro Phe Ile Thr Ser Asn Asn Ser Asn Pro Val Glu
                325                 330                 335
Asp Glu Asp Ala Val Ala Leu Thr Cys Glu Pro Glu Ile Gln Asn Thr
            340                 345                 350
Thr Tyr Leu Trp Trp Val Asn Asn Gln Ser Leu Pro Val Ser Pro Arg
        355                 360                 365
Leu Gln Leu Ser Asn Asp Asn Arg Thr Leu Thr Leu Leu Ser Val Thr
    370                 375                 380
Arg Asn Asp Val Gly Pro Tyr Glu Cys Gly Ile Gln Asn Lys Leu Ser
385                 390                 395                 400
Val Asp His Ser Asp Pro Val Ile Leu Asn Val Leu Tyr Gly Pro Asp
                405                 410                 415
Asp Pro Thr Ile Ser Pro Ser Tyr Thr Tyr Tyr Arg Pro Gly Val Asn
            420                 425                 430
Leu Ser Leu Ser Cys His Ala Ala Ser Asn Pro Pro Ala Gln Tyr Ser
        435                 440                 445
Trp Leu Ile Asp Gly Asn Ile Gln Gln His Thr Gln Glu Leu Phe Ile
    450                 455                 460
Ser Asn Ile Thr Glu Lys Asn Ser Gly Leu Tyr Thr Cys Gln Ala Asn
465                 470                 475                 480
Asn Ser Ala Ser Gly His Ser Arg Thr Thr Val Lys Thr Ile Thr Val
                485                 490                 495
Ser Ala Glu Leu Pro Lys Pro Ser Ile Ser Ser Asn Asn Ser Lys Pro
            500                 505                 510
Val Glu Asp Lys Asp Ala Val Ala Phe Thr Cys Glu Pro Glu Ala Gln
        515                 520                 525
Asn Thr Thr Tyr Leu Trp Trp Val Asn Gly Gln Ser Leu Pro Val Ser
    530                 535                 540
Pro Arg Leu Gln Leu Ser Asn Gly Asn Arg Thr Leu Thr Leu Phe Asn
545                 550                 555                 560
Val Thr Arg Asn Asp Ala Arg Ala Tyr Val Cys Gly Ile Gln Asn Ser
                565                 570                 575
Val Ser Ala Asn Arg Ser Asp Pro Val Thr Leu Asp Val Leu Tyr Gly
```

```
            580             585             590
Pro Asp Thr Pro Ile Ile Ser Pro Pro Asp Ser Ser Tyr Leu Ser Gly
            595             600             605

Ala Asn Leu Asn Leu Ser Cys His Ser Ala Ser Asn Pro Ser Pro Gln
        610             615             620

Tyr Ser Trp Arg Ile Asn Gly Ile Pro Gln Gln His Thr Gln Val Leu
625             630             635             640

Phe Ile Ala Lys Ile Thr Pro Asn Asn Gly Thr Tyr Ala Cys Phe
            645             650             655

Val Ser Asn Leu Ala Thr Gly Arg Asn Asn Ser Ile Val Lys Ser Ile
        660             665             670

Thr Val Ser Ala Ser Gly Thr Ser Pro Gly Leu Ser Ala Gly Ala Thr
    675             680             685

Val Gly Ile Met Ile Gly Val Leu Val Gly Val Ala Leu Ile
        690             695             700

<210> SEQ ID NO 4
<211> LENGTH: 344
<212> TYPE: PRT
<213> ORGANISM: Homo sapiens

<400> SEQUENCE: 4

Met Gly Pro Pro Ser Ala Pro Pro Cys Arg Leu His Val Pro Trp Lys
1               5                   10                  15

Glu Val Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Ala His Asn Leu Pro Gln Asn Arg Ile Gly
    50                  55                  60

Tyr Ser Trp Tyr Lys Gly Glu Arg Val Asp Gly Asn Ser Leu Ile Val
65                  70                  75                  80

Gly Tyr Val Ile Gly Thr Gln Ala Thr Pro Gly Pro Ala Tyr Ser
            85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Val Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Met Thr Leu Thr Leu Ser Val Lys Arg Asn
        195                 200                 205

Asp Ala Gly Ser Tyr Glu Cys Glu Ile Gln Asn Pro Ala Ser Ala Asn
    210                 215                 220

Arg Ser Asp Pro Val Thr Leu Asn Val Leu Tyr Gly Pro Asp Gly Pro
225                 230                 235                 240

Thr Ile Ser Pro Ser Lys Ala Asn Tyr Arg Pro Gly Glu Asn Leu Asn
                245                 250                 255
```

```
Leu Ser Cys His Ala Ala Ser Asn Pro Ala Gln Tyr Ser Trp Phe
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala His Asn Ser
290                 295                 300

Ala Thr Gly Leu Asn Arg Thr Thr Val Thr Met Ile Thr Val Ser Gly
305                 310                 315                 320

Ser Ala Pro Val Leu Ser Ala Val Ala Thr Val Gly Ile Thr Ile Gly
                325                 330                 335

Val Leu Ala Arg Val Ala Leu Ile
            340

<210> SEQ ID NO 5
<211> LENGTH: 207
<212> TYPE: PRT
<213> ORGANISM: Homo sapiens

<400> SEQUENCE: 5

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 6
<211> LENGTH: 404
<212> TYPE: PRT
<213> ORGANISM: Artificial sequence
<220> FEATURE:
<223> OTHER INFORMATION: extracellular domain of human CEACAM1, fused to
      a 10-His tag

<400> SEQUENCE: 6

Gln Leu Thr Thr Glu Ser Met Pro Phe Asn Val Ala Glu Gly Lys Glu
1               5                   10                  15
```

Val Leu Leu Leu Val His Asn Leu Pro Gln Gln Leu Phe Gly Tyr Ser
             20                  25                  30

Trp Tyr Lys Gly Glu Arg Val Asp Gly Asn Arg Gln Ile Val Gly Tyr
         35                  40                  45

Ala Ile Gly Thr Gln Gln Ala Thr Pro Gly Pro Ala Asn Ser Gly Arg
     50                  55                  60

Glu Thr Ile Tyr Pro Asn Ala Ser Leu Leu Ile Gln Asn Val Thr Gln
65                  70                  75                  80

Asn Asp Thr Gly Phe Tyr Thr Leu Gln Val Ile Lys Ser Asp Leu Val
                 85                  90                  95

Asn Glu Glu Ala Thr Gly Gln Phe His Val Tyr Pro Glu Leu Pro Lys
            100                 105                 110

Pro Ser Ile Ser Ser Asn Asn Ser Asn Pro Val Glu Asp Lys Asp Ala
        115                 120                 125

Val Ala Phe Thr Cys Glu Pro Glu Thr Gln Asp Thr Thr Tyr Leu Trp
    130                 135                 140

Trp Ile Asn Asn Gln Ser Leu Pro Val Ser Pro Arg Leu Gln Leu Ser
145                 150                 155                 160

Asn Gly Asn Arg Thr Leu Thr Leu Leu Ser Val Thr Arg Asn Asp Thr
                165                 170                 175

Gly Pro Tyr Glu Cys Glu Ile Gln Asn Pro Val Ser Ala Asn Arg Ser
            180                 185                 190

Asp Pro Val Thr Leu Asn Val Thr Tyr Gly Pro Asp Thr Pro Thr Ile
        195                 200                 205

Ser Pro Ser Asp Thr Tyr Tyr Arg Pro Gly Ala Asn Leu Ser Leu Ser
210                 215                 220

Cys Tyr Ala Ala Ser Asn Pro Pro Ala Gln Tyr Ser Trp Leu Ile Asn
225                 230                 235                 240

Gly Thr Phe Gln Gln Ser Thr Gln Glu Leu Phe Ile Pro Asn Ile Thr
                245                 250                 255

Val Asn Asn Ser Gly Ser Tyr Thr Cys His Ala Asn Asn Ser Val Thr
            260                 265                 270

Gly Cys Asn Arg Thr Thr Val Lys Thr Ile Ile Val Thr Glu Leu Ser
        275                 280                 285

Pro Val Val Ala Lys Pro Gln Ile Lys Ala Ser Lys Thr Thr Val Thr
290                 295                 300

Gly Asp Lys Asp Ser Val Asn Leu Thr Cys Ser Thr Asn Asp Thr Gly
305                 310                 315                 320

Ile Ser Ile Arg Trp Phe Phe Lys Asn Gln Ser Leu Pro Ser Ser Glu
                325                 330                 335

Arg Met Lys Leu Ser Gln Gly Asn Thr Thr Leu Ser Ile Asn Pro Val
            340                 345                 350

Lys Arg Glu Asp Ala Gly Thr Tyr Trp Cys Glu Val Phe Asn Pro Ile
        355                 360                 365

Ser Lys Asn Gln Ser Asp Pro Ile Met Leu Asn Val Asn Tyr Asn Ala
    370                 375                 380

Leu Pro Gln Glu Asn Gly Leu Ser Pro Gly His His His His His
385                 390                 395                 400

His His His His

<210> SEQ ID NO 7
<211> LENGTH: 5
<212> TYPE: PRT
<213> ORGANISM: Artificial Sequence

```
<220> FEATURE:
<223> OTHER INFORMATION: HCDR1

<400> SEQUENCE: 7

Asn Tyr Ala Met Asn
1               5

<210> SEQ ID NO 8
<211> LENGTH: 17
<212> TYPE: PRT
<213> ORGANISM: Artificial Sequence
<220> FEATURE:
<223> OTHER INFORMATION: HCDR2

<400> SEQUENCE: 8

Val Ile Ser Gly Ser Gly Ser Gly Thr Tyr Tyr Ala Asp Ser Val Lys
1               5                   10                  15

Gly

<210> SEQ ID NO 9
<211> LENGTH: 15
<212> TYPE: PRT
<213> ORGANISM: Artificial Sequence
<220> FEATURE:
<223> OTHER INFORMATION: HCDR3

<400> SEQUENCE: 9

Pro Pro Pro Met Val Arg Gly Val Ile Ile Thr Ile Gly Asn Tyr
1               5                   10                  15

<210> SEQ ID NO 10
<211> LENGTH: 11
<212> TYPE: PRT
<213> ORGANISM: Artificial Sequence
<220> FEATURE:
<223> OTHER INFORMATION: LCDR1

<400> SEQUENCE: 10

Arg Ala Ser Gln Ser Val Ser Val Asn Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: LCDR2

<400> SEQUENCE: 11

Gly Ala Ser Thr Arg Ala Thr
1               5

<210> SEQ ID NO 12
<211> LENGTH: 9
<212> TYPE: PRT
<213> ORGANISM: Artificial Sequence
<220> FEATURE:
<223> OTHER INFORMATION: LCDR3

<400> SEQUENCE: 12

Gln Gln Tyr Asn Asn Trp Pro Phe Thr
1               5

<210> SEQ ID NO 13
<211> LENGTH: 5
<212> TYPE: PRT
```

```
<213> ORGANISM: Artificial Sequence
<220> FEATURE:
<223> OTHER INFORMATION: HCDR1

<400> SEQUENCE: 13

Ser Tyr Gly Leu Ser
1               5

<210> SEQ ID NO 14
<211> LENGTH: 17
<212> TYPE: PRT
<213> ORGANISM: Artificial Sequence
<220> FEATURE:
<223> OTHER INFORMATION: HCDR2

<400> SEQUENCE: 14

Trp Ile Asn Thr Asn Thr Gly Asn Pro Thr Tyr Ala Gln Gly Phe Thr
1               5                   10                  15
Gly

<210> SEQ ID NO 15
<211> LENGTH: 9
<212> TYPE: PRT
<213> ORGANISM: Artificial Sequence
<220> FEATURE:
<223> OTHER INFORMATION: HCDR3

<400> SEQUENCE: 15

Lys Gly Ile Trp Gly Pro Phe Asp Tyr
1               5

<210> SEQ ID NO 16
<211> LENGTH: 17
<212> TYPE: PRT
<213> ORGANISM: Artificial Sequence
<220> FEATURE:
<223> OTHER INFORMATION: LCDR1

<400> SEQUENCE: 16

Lys Ser Ser Gln Asn Val Leu Tyr Ser Ser Asn Asn Lys Asn Tyr Leu
1               5                   10                  15
Ala

<210> SEQ ID NO 17
<211> LENGTH: 7
<212> TYPE: PRT
<213> ORGANISM: Artificial Sequence
<220> FEATURE:
<223> OTHER INFORMATION: LCDR2

<400> SEQUENCE: 17

Trp Ala Ser Thr Arg Glu Ser
1               5

<210> SEQ ID NO 18
<211> LENGTH: 9
<212> TYPE: PRT
<213> ORGANISM: Artificial Sequence
<220> FEATURE:
<223> OTHER INFORMATION: LCDR3

<400> SEQUENCE: 18

Gln Gln Tyr Phe Ser Ser Pro Trp Thr
1               5
```

```
<210> SEQ ID NO 19
<211> LENGTH: 5
<212> TYPE: PRT
<213> ORGANISM: Artificial Sequence
<220> FEATURE:
<223> OTHER INFORMATION: HCDR1

<400> SEQUENCE: 19

Asn Tyr Gly Val Asn
1               5

<210> SEQ ID NO 20
<211> LENGTH: 17
<212> TYPE: PRT
<213> ORGANISM: Artificial Sequence
<220> FEATURE:
<223> OTHER INFORMATION: HCDR2

<400> SEQUENCE: 20

Trp Ile Asn Thr Asn Thr Gly Asn Pro Thr Tyr Val Gln Gly Phe Thr
1               5                   10                  15

Gly

<210> SEQ ID NO 21
<211> LENGTH: 9
<212> TYPE: PRT
<213> ORGANISM: Artificial Sequence
<220> FEATURE:
<223> OTHER INFORMATION: HCDR3

<400> SEQUENCE: 21

Lys Gly Ile Trp Gly Pro Phe Asp His
1               5

<210> SEQ ID NO 22
<211> LENGTH: 17
<212> TYPE: PRT
<213> ORGANISM: Artificial Sequence
<220> FEATURE:
<223> OTHER INFORMATION: LCDR1

<400> SEQUENCE: 22

Lys Ser Ser Gln Ser Val Leu Tyr Ser Ser Asn Asn Arg Leu Tyr Leu
1               5                   10                  15

Ala

<210> SEQ ID NO 23
<211> LENGTH: 7
<212> TYPE: PRT
<213> ORGANISM: Artificial Sequence
<220> FEATURE:
<223> OTHER INFORMATION: LCDR2

<400> SEQUENCE: 23

Trp Ala Ser Thr Arg Glu Ser
1               5

<210> SEQ ID NO 24
<211> LENGTH: 9
<212> TYPE: PRT
<213> ORGANISM: Artificial Sequence
<220> FEATURE:
<223> OTHER INFORMATION: LCDR3

<400> SEQUENCE: 24

Gln Gln Tyr Tyr Ser Asn Pro Trp Thr
```

```
<210> SEQ ID NO 25
<211> LENGTH: 5
<212> TYPE: PRT
<213> ORGANISM: Artificial Sequence
<220> FEATURE:
<223> OTHER INFORMATION: HCDR1

<400> SEQUENCE: 25

Asn Tyr Ala Met Asn
1               5

<210> SEQ ID NO 26
<211> LENGTH: 17
<212> TYPE: PRT
<213> ORGANISM: Artificial Sequence
<220> FEATURE:
<223> OTHER INFORMATION: HCDR2

<400> SEQUENCE: 26

Val Ile Ser Gly Ser Gly Ser Gly Thr Tyr Tyr Ala Asp Ser Val Lys
1               5                   10                  15

Gly

<210> SEQ ID NO 27
<211> LENGTH: 15
<212> TYPE: PRT
<213> ORGANISM: Artificial Sequence
<220> FEATURE:
<223> OTHER INFORMATION: HCDR3

<400> SEQUENCE: 27

Pro Pro Pro Met Val Arg Gly Val Ile Ile Thr Ile Gly Asn Tyr
1               5                   10                  15

<210> SEQ ID NO 28
<211> LENGTH: 11
<212> TYPE: PRT
<213> ORGANISM: Artificial Sequence
<220> FEATURE:
<223> OTHER INFORMATION: LCDR1

<400> SEQUENCE: 28

Arg Ala Ser Gln Ser Val Ser Val Asn Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: LCDR2

<400> SEQUENCE: 29

Gly Ala Ser Thr Arg Ala Thr
1               5

<210> SEQ ID NO 30
<211> LENGTH: 9
<212> TYPE: PRT
<213> ORGANISM: Artificial Sequence
<220> FEATURE:
<223> OTHER INFORMATION: LCDR3

<400> SEQUENCE: 30
```

Gln Gln Tyr Asn Asn Trp Pro Phe Thr
1               5

<210> SEQ ID NO 31
<211> LENGTH: 7
<212> TYPE: PRT
<213> ORGANISM: Artificial Sequence
<220> FEATURE:
<223> OTHER INFORMATION: HCDR1

<400> SEQUENCE: 31

Ser Gly Gly His Tyr Trp Ser
1               5

<210> SEQ ID NO 32
<211> LENGTH: 16
<212> TYPE: PRT
<213> ORGANISM: Artificial Sequence
<220> FEATURE:
<223> OTHER INFORMATION: HCDR2

<400> SEQUENCE: 32

Asn Ile Tyr Tyr Ser Gly Ser Thr His Tyr Asn Pro Ser Leu Lys Ser
1               5                   10                  15

<210> SEQ ID NO 33
<211> LENGTH: 14
<212> TYPE: PRT
<213> ORGANISM: Artificial Sequence
<220> FEATURE:
<223> OTHER INFORMATION: HCDR3

<400> SEQUENCE: 33

Gly Arg Leu Leu Trp Phe Gly Glu Pro Gln Asp Phe Gln His
1               5                   10

<210> SEQ ID NO 34
<211> LENGTH: 17
<212> TYPE: PRT
<213> ORGANISM: Artificial Sequence
<220> FEATURE:
<223> OTHER INFORMATION: LCDR1

<400> SEQUENCE: 34

Lys Ser Ser Gln Ser Val Leu Tyr Ser Ser Asn Asn Lys Asn Tyr Leu
1               5                   10                  15

Thr

<210> SEQ ID NO 35
<211> LENGTH: 7
<212> TYPE: PRT
<213> ORGANISM: Artificial Sequence
<220> FEATURE:
<223> OTHER INFORMATION: LCDR2

<400> SEQUENCE: 35

Trp Ala Ser Thr Arg Glu Ser
1               5

<210> SEQ ID NO 36
<211> LENGTH: 8
<212> TYPE: PRT
<213> ORGANISM: Artificial Sequence
<220> FEATURE:
<223> OTHER INFORMATION: LCDR3

<400> SEQUENCE: 36

Gln Gln Tyr Tyr Ser Thr Pro Thr
1               5

<210> SEQ ID NO 37
<211> LENGTH: 5
<212> TYPE: PRT
<213> ORGANISM: Artificial Sequence
<220> FEATURE:
<223> OTHER INFORMATION: HCDR1

<400> SEQUENCE: 37

Asp Tyr Gly Met Asn
1               5

<210> SEQ ID NO 38
<211> LENGTH: 17
<212> TYPE: PRT
<213> ORGANISM: Artificial Sequence
<220> FEATURE:
<223> OTHER INFORMATION: HCDR2

<400> SEQUENCE: 38

Trp Ile Asn Thr Asn Thr Gly Asn Pro Thr Tyr Ala Gln Gly Phe Thr
1               5                   10                  15

Gly

<210> SEQ ID NO 39
<211> LENGTH: 9
<212> TYPE: PRT
<213> ORGANISM: Artificial Sequence
<220> FEATURE:
<223> OTHER INFORMATION: HCDR3

<400> SEQUENCE: 39

Lys Ala Ile Trp Gly Trp Phe Asp Pro
1               5

<210> SEQ ID NO 40
<211> LENGTH: 17
<212> TYPE: PRT
<213> ORGANISM: Artificial Sequence
<220> FEATURE:
<223> OTHER INFORMATION: LCDR1

<400> SEQUENCE: 40

Lys Pro Ser Gln Ser Val Leu Tyr Arg Ser Asn Asn Lys Asn Tyr Leu
1               5                   10                  15

Ala

<210> SEQ ID NO 41
<211> LENGTH: 7
<212> TYPE: PRT
<213> ORGANISM: Artificial Sequence
<220> FEATURE:
<223> OTHER INFORMATION: LCDR2

<400> SEQUENCE: 41

Trp Ala Ser Thr Arg Glu Ser
1               5

<210> SEQ ID NO 42
<211> LENGTH: 9
<212> TYPE: PRT
<213> ORGANISM: Artificial Sequence
<220> FEATURE:

```
<223> OTHER INFORMATION: LCDR3

<400> SEQUENCE: 42

Gln Gln Tyr Tyr Ser Thr Pro Cys Ser
1               5

<210> SEQ ID NO 43
<211> LENGTH: 5
<212> TYPE: PRT
<213> ORGANISM: Artificial Sequence
<220> FEATURE:
<223> OTHER INFORMATION: HCDR1

<400> SEQUENCE: 43

Asn Tyr Ala Met Thr
1               5

<210> SEQ ID NO 44
<211> LENGTH: 17
<212> TYPE: PRT
<213> ORGANISM: Artificial Sequence
<220> FEATURE:
<223> OTHER INFORMATION: HCDR2

<400> SEQUENCE: 44

Ser Ile Ser Gly Thr Ser Ala Asn Thr Tyr Tyr Ala Asp Ala Val Lys
1               5                   10                  15

Gly

<210> SEQ ID NO 45
<211> LENGTH: 13
<212> TYPE: PRT
<213> ORGANISM: Artificial Sequence
<220> FEATURE:
<223> OTHER INFORMATION: HCDR3

<400> SEQUENCE: 45

Pro Ile Leu Thr Leu Phe Gly Glu Leu Pro Leu Asp Tyr
1               5                   10

<210> SEQ ID NO 46
<211> LENGTH: 11
<212> TYPE: PRT
<213> ORGANISM: Artificial Sequence
<220> FEATURE:
<223> OTHER INFORMATION: LCDR1

<400> SEQUENCE: 46

Arg Ala Ser Gln Ser Val Ser Ser Asn Leu Ala
1               5                   10

<210> SEQ ID NO 47
<211> LENGTH: 7
<212> TYPE: PRT
<213> ORGANISM: Artificial Sequence
<220> FEATURE:
<223> OTHER INFORMATION: LCDR2

<400> SEQUENCE: 47

Gly Ala Ser Thr Arg Ala Thr
1               5

<210> SEQ ID NO 48
<211> LENGTH: 9
<212> TYPE: PRT
<213> ORGANISM: Artificial Sequence
```

```
<220> FEATURE:
<223> OTHER INFORMATION: LCDR3

<400> SEQUENCE: 48

Gln Gln Tyr Asn Asn Trp Pro Leu Thr
1               5

<210> SEQ ID NO 49
<211> LENGTH: 7
<212> TYPE: PRT
<213> ORGANISM: Artificial Sequence
<220> FEATURE:
<223> OTHER INFORMATION: HCDR1

<400> SEQUENCE: 49

Arg Thr Ser Tyr Tyr Trp Gly
1               5

<210> SEQ ID NO 50
<211> LENGTH: 16
<212> TYPE: PRT
<213> ORGANISM: Artificial Sequence
<220> FEATURE:
<223> OTHER INFORMATION: HCDR2

<400> SEQUENCE: 50

Thr Ile Tyr Tyr Ser Gly Ser Thr Tyr Tyr Asn Pro Ser Leu Lys Ser
1               5                   10                  15

<210> SEQ ID NO 51
<211> LENGTH: 11
<212> TYPE: PRT
<213> ORGANISM: Artificial Sequence
<220> FEATURE:
<223> OTHER INFORMATION: HCDR3

<400> SEQUENCE: 51

Gln Ile Ala Val Gly Ala His Arg Phe Asp Tyr
1               5                   10

<210> SEQ ID NO 52
<211> LENGTH: 11
<212> TYPE: PRT
<213> ORGANISM: Artificial Sequence
<220> FEATURE:
<223> OTHER INFORMATION: LCDR1

<400> SEQUENCE: 52

Arg Ala Ser Gln Gly Ile Ser Ser Tyr Leu Ala
1               5                   10

<210> SEQ ID NO 53
<211> LENGTH: 7
<212> TYPE: PRT
<213> ORGANISM: Artificial Sequence
<220> FEATURE:
<223> OTHER INFORMATION: LCDR2

<400> SEQUENCE: 53

Ala Ala Ser Thr Leu Gln Ser
1               5

<210> SEQ ID NO 54
<211> LENGTH: 9
<212> TYPE: PRT
<213> ORGANISM: Artificial Sequence
<220> FEATURE:
```

```
<223> OTHER INFORMATION: LCDR3

<400> SEQUENCE: 54

Gln Gln Leu Asn Ser Tyr Pro Trp Thr
1               5

<210> SEQ ID NO 55
<211> LENGTH: 5
<212> TYPE: PRT
<213> ORGANISM: Artificial Sequence
<220> FEATURE:
<223> OTHER INFORMATION: HCDR1

<400> SEQUENCE: 55

Asp Tyr Ala Met Asn
1               5

<210> SEQ ID NO 56
<211> LENGTH: 17
<212> TYPE: PRT
<213> ORGANISM: Artificial Sequence
<220> FEATURE:
<223> OTHER INFORMATION: HCDR2

<400> SEQUENCE: 56

Ser Ile Ser Gly Thr Gly Gly Ser Thr Tyr Tyr Ala Asp Ser Leu Lys
1               5                   10                  15

Gly

<210> SEQ ID NO 57
<211> LENGTH: 12
<212> TYPE: PRT
<213> ORGANISM: Artificial Sequence
<220> FEATURE:
<223> OTHER INFORMATION: HCDR3

<400> SEQUENCE: 57

Asp Ile Ala Val Gly Val Thr Ala Tyr Phe Asp His
1               5                   10

<210> SEQ ID NO 58
<211> LENGTH: 11
<212> TYPE: PRT
<213> ORGANISM: Artificial Sequence
<220> FEATURE:
<223> OTHER INFORMATION: LCDR1

<400> SEQUENCE: 58

Gln Gly Asp Ser Leu Arg Thr Tyr Ser Ala Ser
1               5                   10

<210> SEQ ID NO 59
<211> LENGTH: 7
<212> TYPE: PRT
<213> ORGANISM: Artificial Sequence
<220> FEATURE:
<223> OTHER INFORMATION: LCDR2

<400> SEQUENCE: 59

Gly Lys Asn Asn Arg Pro Ser
1               5

<210> SEQ ID NO 60
<211> LENGTH: 12
<212> TYPE: PRT
<213> ORGANISM: Artificial Sequence
```

```
<220> FEATURE:
<223> OTHER INFORMATION: LCDR3

<400> SEQUENCE: 60

Asn Ser Arg Asp Ser Arg Gly Asn Leu Leu Val Val
1               5                   10

<210> SEQ ID NO 61
<211> LENGTH: 5
<212> TYPE: PRT
<213> ORGANISM: Artificial Sequence
<220> FEATURE:
<223> OTHER INFORMATION: HCDR1

<400> SEQUENCE: 61

Thr Tyr Gly Met Ser
1               5

<210> SEQ ID NO 62
<211> LENGTH: 17
<212> TYPE: PRT
<213> ORGANISM: Artificial Sequence
<220> FEATURE:
<223> OTHER INFORMATION: HCDR2

<400> SEQUENCE: 62

Thr Ile Ser Gly Ser Gly Asp Asn Thr Tyr Tyr Ala Asp Ser Val Lys
1               5                   10                  15

Gly

<210> SEQ ID NO 63
<211> LENGTH: 15
<212> TYPE: PRT
<213> ORGANISM: Artificial Sequence
<220> FEATURE:
<223> OTHER INFORMATION: HCDR3

<400> SEQUENCE: 63

Gly Gly Leu Leu Trp Phe Gly Glu Leu Pro Tyr Pro Phe Asp Tyr
1               5                   10                  15

<210> SEQ ID NO 64
<211> LENGTH: 14
<212> TYPE: PRT
<213> ORGANISM: Artificial Sequence
<220> FEATURE:
<223> OTHER INFORMATION: LCDR1

<400> SEQUENCE: 64

Thr Gly Thr Ser Ser Asp Val Gly Gly Tyr Asn Tyr Val Ser
1               5                   10

<210> SEQ ID NO 65
<211> LENGTH: 7
<212> TYPE: PRT
<213> ORGANISM: Artificial Sequence
<220> FEATURE:
<223> OTHER INFORMATION: LCDR2

<400> SEQUENCE: 65

Asp Val Ser Asn Arg Pro Ser
1               5

<210> SEQ ID NO 66
<211> LENGTH: 11
<212> TYPE: PRT
```

```
<213> ORGANISM: Artificial Sequence
<220> FEATURE:
<223> OTHER INFORMATION: LCDR3

<400> SEQUENCE: 66

Ser Ser Tyr Ile Ser Thr Ser Thr Leu Tyr Val
1               5                   10

<210> SEQ ID NO 67
<211> LENGTH: 5
<212> TYPE: PRT
<213> ORGANISM: Artificial Sequence
<220> FEATURE:
<223> OTHER INFORMATION: HCDR1

<400> SEQUENCE: 67

Ser Tyr Ala Met Asn
1               5

<210> SEQ ID NO 68
<211> LENGTH: 17
<212> TYPE: PRT
<213> ORGANISM: Artificial Sequence
<220> FEATURE:
<223> OTHER INFORMATION: HCDR2

<400> SEQUENCE: 68

Ala Ile Ser Gly Ser Gly Gly Ser Thr Tyr Tyr Ala Asp Ser Val Lys
1               5                   10                  15

Gly

<210> SEQ ID NO 69
<211> LENGTH: 12
<212> TYPE: PRT
<213> ORGANISM: Artificial Sequence
<220> FEATURE:
<223> OTHER INFORMATION: HCDR3

<400> SEQUENCE: 69

Asp Phe Ala Val Gly Ala Thr Thr Ser Phe Asp Tyr
1               5                   10

<210> SEQ ID NO 70
<211> LENGTH: 11
<212> TYPE: PRT
<213> ORGANISM: Artificial Sequence
<220> FEATURE:
<223> OTHER INFORMATION: LCDR1

<400> SEQUENCE: 70

Gln Gly Asp Ser Leu Arg Ser Tyr Tyr Val Ser
1               5                   10

<210> SEQ ID NO 71
<211> LENGTH: 7
<212> TYPE: PRT
<213> ORGANISM: Artificial Sequence
<220> FEATURE:
<223> OTHER INFORMATION: LCDR2

<400> SEQUENCE: 71

Gly Lys Asn Asn Arg Pro Ser
1               5

<210> SEQ ID NO 72
<211> LENGTH: 11
```

```
<212> TYPE: PRT
<213> ORGANISM: Artificial Sequence
<220> FEATURE:
<223> OTHER INFORMATION: LCDR3

<400> SEQUENCE: 72

Asn Ser Arg Asp Ser Ser Asn His Leu Val Val
1               5                   10

<210> SEQ ID NO 73
<211> LENGTH: 5
<212> TYPE: PRT
<213> ORGANISM: Artificial Sequence
<220> FEATURE:
<223> OTHER INFORMATION: HCDR1

<400> SEQUENCE: 73

Ser Tyr Trp Ile Gly
1               5

<210> SEQ ID NO 74
<211> LENGTH: 17
<212> TYPE: PRT
<213> ORGANISM: Artificial Sequence
<220> FEATURE:
<223> OTHER INFORMATION: HCDR2

<400> SEQUENCE: 74

Ile Ile Tyr Pro Gly Asp Ser Asp Thr Arg Tyr Ser Pro Ser Phe Gln
1               5                   10                  15

Gly

<210> SEQ ID NO 75
<211> LENGTH: 12
<212> TYPE: PRT
<213> ORGANISM: Artificial Sequence
<220> FEATURE:
<223> OTHER INFORMATION: HCDR3

<400> SEQUENCE: 75

Gly Tyr Pro Ala Pro Thr Val Asn Asp Leu Asp Tyr
1               5                   10

<210> SEQ ID NO 76
<211> LENGTH: 11
<212> TYPE: PRT
<213> ORGANISM: Artificial Sequence
<220> FEATURE:
<223> OTHER INFORMATION: LCDR1

<400> SEQUENCE: 76

Arg Ala Ser Gln Ser Ile Ser Ser Tyr Leu Asn
1               5                   10

<210> SEQ ID NO 77
<211> LENGTH: 7
<212> TYPE: PRT
<213> ORGANISM: Artificial Sequence
<220> FEATURE:
<223> OTHER INFORMATION: LCDR2

<400> SEQUENCE: 77

Ala Ala Ser Ser Leu Gln Ser
1               5

<210> SEQ ID NO 78
```

```
<211> LENGTH: 9
<212> TYPE: PRT
<213> ORGANISM: Artificial Sequence
<220> FEATURE:
<223> OTHER INFORMATION: LCDR3

<400> SEQUENCE: 78

Gln Gln Ser Tyr Ser Thr Pro Leu Thr
1               5

<210> SEQ ID NO 79
<211> LENGTH: 124
<212> TYPE: PRT
<213> ORGANISM: Artificial Sequence
<220> FEATURE:
<223> OTHER INFORMATION: CCMB02 VH

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ile Asn Tyr
            20                  25                  30

Ala Met Asn Trp Val Arg Leu Thr Pro Gly Lys Gly Leu Glu Trp Val
        35                  40                  45

Ser Val Ile Ser Gly Ser Gly Ser Thr Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Val Glu Asp Thr Ala Ile Tyr Tyr Cys
                85                  90                  95

Ala Ser Pro Pro Met Val Arg Gly Val Ile Ile Thr Ile Gly Asn
            100                 105                 110

Tyr Trp Gly Gln Gly Ala Leu Val Thr Val Ser Ser
            115                 120

<210> SEQ ID NO 80
<211> LENGTH: 107
<212> TYPE: PRT
<213> ORGANISM: Artificial Sequence
<220> FEATURE:
<223> OTHER INFORMATION: CCMB02 VL

<400> SEQUENCE: 80

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Val Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Phe
                85                  90                  95

Thr Phe Gly Pro Gly Thr Lys Val Asp Ile Lys
            100                 105

<210> SEQ ID NO 81
<211> LENGTH: 118
```

<212> TYPE: PRT
<213> ORGANISM: Artificial Sequence
<220> FEATURE:
<223> OTHER INFORMATION: CCMB03 VH

<400> SEQUENCE: 81

Gln Val Gln Leu Val Gln Ser Gly Ser Glu Leu Arg Thr Pro Gly Ala
1               5                   10                  15

Ser Val Lys Val Ser Cys Lys Ala Ser Gly Tyr Thr Phe Thr Ser Tyr
            20                  25                  30

Gly Leu Ser Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Lys Gly Ile Trp Gly Pro Phe Asp Tyr Trp Gly Gln Gly Thr
            100                 105                 110

Leu Val Thr Val Ser Ser
        115

<210> SEQ ID NO 82
<211> LENGTH: 113
<212> TYPE: PRT
<213> ORGANISM: Artificial Sequence
<220> FEATURE:
<223> OTHER INFORMATION: CCMB03 VL

<400> SEQUENCE: 82

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asn Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Cys Leu Gln Ala Glu Asp Val Ala Val Tyr Tyr Cys Gln Gln
                85                  90                  95

Tyr Phe Ser Ser Pro Trp Thr Phe Gly Gln Gly Thr Lys Val Glu Ile
            100                 105                 110

Lys

<210> SEQ ID NO 83
<211> LENGTH: 118
<212> TYPE: PRT
<213> ORGANISM: Artificial Sequence
<220> FEATURE:
<223> OTHER INFORMATION: CCMB04 VH

<400> SEQUENCE: 83

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

```
Gly Val Asn Trp Val Arg Gln Ala Pro Gly Gln Gly Leu Glu Trp Met
            35                  40                  45

Gly Trp Ile Asn Thr Asn Thr Gly Asn Pro Thr Tyr Val Gln Gly Phe
        50                  55                  60

Thr Gly Arg Phe Val Phe Ser Leu Asp Thr Ser Val Thr Thr Ala Tyr
 65                  70                  75                  80

Leu His Ile Ser Ser Leu Lys Ala Glu Asp Thr Ala Val Tyr Phe Cys
                85                  90                  95

Ala Arg Lys Gly Ile Trp Gly Pro Phe Asp His Trp Gly Gln Gly Thr
            100                 105                 110

Leu Val Thr Val Ser Ser
            115
```

<210> SEQ ID NO 84
<211> LENGTH: 113
<212> TYPE: PRT
<213> ORGANISM: Artificial Sequence
<220> FEATURE:
<223> OTHER INFORMATION: CCMB04 VL

<400> SEQUENCE: 84

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Arg Leu Tyr Leu Ala Trp Tyr Gln Gln Arg Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Ser Asn Pro Trp Thr Phe Gly Gly Gly Thr Lys Val Glu Ile
            100                 105                 110

Lys
```

<210> SEQ ID NO 85
<211> LENGTH: 124
<212> TYPE: PRT
<213> ORGANISM: Artificial Sequence
<220> FEATURE:
<223> OTHER INFORMATION: CCMB07 VH

<400> SEQUENCE: 85

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Asn Tyr
            20                  25                  30

Ala Met Asn Trp Val Arg Leu Ala Pro Gly Lys Gly Leu Glu Trp Val
            35                  40                  45

Ser Val Ile Ser Gly Ser Gly Gly Thr Tyr Tyr Ala Asp Ser Val
        50                  55                  60

Lys Gly Arg Phe Thr Val Ser Arg Asp Asn Ser Lys Asn Thr Leu Tyr
 65                  70                  75                  80

Leu Gln Met Asn Ser Leu Arg Val Glu Asp Thr Ala Ile Tyr Tyr Cys
                85                  90                  95
```

Ala Ser Pro Pro Met Val Arg Gly Val Ile Ile Thr Ile Gly Asn
                100                 105                 110

Tyr Trp Gly Gln Gly Ala Leu Val Thr Val Ser Ser
        115                 120

<210> SEQ ID NO 86
<211> LENGTH: 107
<212> TYPE: PRT
<213> ORGANISM: Artificial Sequence
<220> FEATURE:
<223> OTHER INFORMATION: CCMB07 VL

<400> SEQUENCE: 86

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Val Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Ser Ile Pro Thr Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Phe
                85                  90                  95

Thr Phe Gly Pro Gly Thr Lys Val Glu Ile Lys
            100                 105

<210> SEQ ID NO 87
<211> LENGTH: 124
<212> TYPE: PRT
<213> ORGANISM: Artificial Sequence
<220> FEATURE:
<223> OTHER INFORMATION: CCMB09 VH

<400> SEQUENCE: 87

Gln Val Gln Leu Gln Glu Ser Gly Pro Gly Leu Val Lys Pro Ser Gln
1               5                   10                  15

Thr Leu Ser Leu Thr Cys Thr Val Thr Gly Asp Ser Ile Arg Ser Gly
            20                  25                  30

Gly Tyr His Tyr Trp Ser Trp Ile Arg Gln His Pro Gly Lys Gly Leu Glu
        35                  40                  45

Trp Ile Gly Asn Ile Tyr Tyr Ser Gly Ser Thr His Tyr Asn Pro Ser
    50                  55                  60

Leu Lys Ser Arg Leu Thr Ile Ser Val Asp Thr Ser Lys Asn Gln Phe
65                  70                  75                  80

Ser Leu Lys Val Ser Ser Val Thr Ala Ala Asp Thr Ala Val Tyr Tyr
                85                  90                  95

Cys Ala Arg Gly Arg Leu Leu Trp Phe Gly Glu Pro Gln Asp Phe Gln
            100                 105                 110

His Trp Gly Gln Gly Thr Leu Val Thr Val Ser Ser
        115                 120

<210> SEQ ID NO 88
<211> LENGTH: 112
<212> TYPE: PRT
<213> ORGANISM: Artificial Sequence
<220> FEATURE:
<223> OTHER INFORMATION: CCMB09 VL

```
<400> SEQUENCE: 88

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Val Leu Tyr Ser
            20                  25                  30

Ser Asn Asn Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Thr Phe Gly Gln Gly Thr Lys Leu Glu Ile Lys
            100                 105                 110

<210> SEQ ID NO 89
<211> LENGTH: 118
<212> TYPE: PRT
<213> ORGANISM: Artificial Sequence
<220> FEATURE:
<223> OTHER INFORMATION: CCMB18 VH

<400> SEQUENCE: 89

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Leu Thr Asp Tyr
            20                  25                  30

Gly Met Asn Trp Val Arg Gln Ala Pro Gly Gln Gly Leu Gln Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Lys Ala Ile Trp Gly Trp Phe Asp Pro Trp Gly Gln Gly Thr
            100                 105                 110

Leu Val Thr Val Ser Ser
        115

<210> SEQ ID NO 90
<211> LENGTH: 113
<212> TYPE: PRT
<213> ORGANISM: Artificial Sequence
<220> FEATURE:
<223> OTHER INFORMATION: CCMB18 VL

<400> SEQUENCE: 90

Asp Ile Val Met Thr Gln Ser Pro Asp Ser Leu Ala Val Ser Leu Gly
1               5                   10                  15

Glu Arg Ala Thr Ile Asn Cys Lys Pro Ser Gln Ser Val Leu Tyr Arg
            20                  25                  30

Ser Asn Asn Lys Asn Tyr Leu Ala Trp Tyr Gln Gln Lys Pro Gly Gln
        35                  40                  45

Pro Pro Lys Leu Leu Ile His Trp Ala Ser Thr Arg Glu Ser Gly Val
    50                  55                  60
```

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
            85                  90                  95

Tyr Tyr Ser Thr Pro Cys Ser Phe Gly Gln Gly Thr Lys Leu Glu Ile
            100                 105                 110

Lys

<210> SEQ ID NO 91
<211> LENGTH: 122
<212> TYPE: PRT
<213> ORGANISM: Artificial Sequence
<220> FEATURE:
<223> OTHER INFORMATION: CCMB20 VH

<400> SEQUENCE: 91

Glu Val Gln Leu Leu Glu Ser Gly Gly Gly Leu Val Gln Pro Gly Glu
1               5                   10                  15

Ser Leu Arg Leu Ser Cys Ala Ala Ser Gly Phe Thr Phe Asn Asn Tyr
            20                  25                  30

Ala Met Thr Trp Val Arg Gln Ala Pro Gly Lys Gly Leu Asp Trp Val
        35                  40                  45

Ser Ser Ile Ser Gly Thr Ser Ala Asn Thr Tyr Tyr Ala Asp Ala Val
    50                  55                  60

Lys Gly Arg Phe Thr Ile Ser Arg Asp Asn Ser Met Thr Thr Leu Tyr
65                  70                  75                  80

Leu Gln Met Asn Ser Leu Arg Ala Glu Asp Thr Ala Val Tyr Tyr Cys
            85                  90                  95

Ala Lys Pro Ile Leu Thr Leu Phe Gly Glu Leu Pro Leu Asp Tyr Trp
            100                 105                 110

Gly Gln Gly Thr Leu Val Thr Val Ser Ser
        115                 120

<210> SEQ ID NO 92
<211> LENGTH: 107
<212> TYPE: PRT
<213> ORGANISM: Artificial Sequence
<220> FEATURE:
<223> OTHER INFORMATION: CCMB20 VL

<400> SEQUENCE: 92

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Thr Gly Gln Ala Pro Arg Leu Leu Ile
        35                  40                  45

Tyr Gly Ala Ser Thr Arg Ala Thr Ala Phe Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
            85                  90                  95

Thr Phe Gly Gly Gly Thr Lys Val Glu Ile Lys
            100                 105

<210> SEQ ID NO 93

```
<211> LENGTH: 121
<212> TYPE: PRT
<213> ORGANISM: Artificial Sequence
<220> FEATURE:
<223> OTHER INFORMATION: CCMB23 VH

<400> SEQUENCE: 93

Gln Leu Gln Leu Gln Glu Ser Gly Pro Gly Leu Val Lys Pro Ser Glu
1               5                   10                  15

Thr Leu Ser Leu Thr Cys Thr Val Ser Ala Asp Ser Ile Ser Arg Thr
            20                  25                  30

Ser Tyr Tyr Trp Gly Trp Ile Arg Gln Pro Pro Gly Lys Gly Leu Glu
        35                  40                  45

Trp Ile Gly Thr Ile Tyr Tyr Ser Gly Ser Thr Tyr Tyr Asn Pro Ser
50                  55                  60

Leu Lys Ser Arg Val Thr Ile Ser Val Asp Thr Ser Arg Asn His Phe
65                  70                  75                  80

Ser Leu Thr Leu Asn Ser Val Thr Ala Ala Asp Thr Ala Val Tyr Tyr
            85                  90                  95

Cys Ala Arg Gln Ile Ala Val Gly Ala His Arg Phe Asp Tyr Trp Gly
            100                 105                 110

Gln Gly Thr Leu Val Thr Val Ser Ser
        115                 120

<210> SEQ ID NO 94
<211> LENGTH: 107
<212> TYPE: PRT
<213> ORGANISM: Artificial Sequence
<220> FEATURE:
<223> OTHER INFORMATION: CCMB23 VL

<400> SEQUENCE: 94

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Trp
            85                  90                  95

Thr Phe Gly Gln Gly Thr Lys Val Glu Ile Lys
        100                 105

<210> SEQ ID NO 95
<211> LENGTH: 121
<212> TYPE: PRT
<213> ORGANISM: Artificial Sequence
<220> FEATURE:
<223> OTHER INFORMATION: CCMB35 VH

<400> SEQUENCE: 95

Glu Val Gln Leu Leu Glu Ser Gly Gly Gly Leu Val Gln Pro Gly Glu
1               5                   10                  15

Ser Leu Arg Leu Ser Cys Ala Ala Ser Gly Leu Thr Phe Ser Asp Tyr
            20                  25                  30
```

```
Ala Met Asn Trp Val Arg Gln Ala Pro Gly Lys Gly Leu Tyr Trp Val
            35                  40                  45

Ser Ser Ile Ser Gly Thr Gly Gly Ser Thr Tyr Tyr Ala Asp Ser Leu
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Ile Ala Val Gly Val Thr Ala Tyr Phe Asp His Trp Gly
            100                 105                 110

Gln Gly Thr Leu Val Thr Val Ser Ser
            115                 120

<210> SEQ ID NO 96
<211> LENGTH: 109
<212> TYPE: PRT
<213> ORGANISM: Artificial Sequence
<220> FEATURE:
<223> OTHER INFORMATION: CCMB35 VL

<400> SEQUENCE: 96

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Thr Tyr Ser Ala
            20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Arg Gly Asn Leu
                85                  90                  95

Leu Val Val Phe Gly Gly Gly Thr Lys Leu Thr Val Leu
            100                 105

<210> SEQ ID NO 97
<211> LENGTH: 124
<212> TYPE: PRT
<213> ORGANISM: Artificial Sequence
<220> FEATURE:
<223> OTHER INFORMATION: CCMB42 VH

<400> SEQUENCE: 97

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
            20                  25                  30

Gly Met Ser Trp Ala Arg Gln Ala Pro Gly Lys Gly Leu Glu Trp Val
            35                  40                  45

Ser Thr Ile Ser Gly Ser Gly Asp Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Ile Asn Ser Leu Arg Ala Glu Asp Thr Ala Val Tyr Tyr Cys
                85                  90                  95

Ala Lys Gly Gly Leu Leu Trp Phe Gly Glu Leu Pro Tyr Pro Phe Asp
            100                 105                 110
```

Tyr Trp Gly Gln Gly Thr Leu Val Thr Val Ser Ser
            115                 120

<210> SEQ ID NO 98
<211> LENGTH: 111
<212> TYPE: PRT
<213> ORGANISM: Artificial Sequence
<220> FEATURE:
<223> OTHER INFORMATION: CCMB42 VL

<400> SEQUENCE: 98

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Asp Asn Thr Ala Ser Leu Thr Ile Ser Gly Leu
65                  70                  75                  80

Gln Ala Glu Asp Glu Ala Asp Tyr Tyr Cys Ser Ser Tyr Ile Ser Thr
                85                  90                  95

Ser Thr Leu Tyr Val Phe Gly Ile Gly Thr Lys Val Thr Val Leu
            100                 105                 110

<210> SEQ ID NO 99
<211> LENGTH: 121
<212> TYPE: PRT
<213> ORGANISM: Artificial Sequence
<220> FEATURE:
<223> OTHER INFORMATION: CCMB61 VH

<400> SEQUENCE: 99

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ala Val Gly Ala Thr Thr Ser Phe Asp Tyr Trp Gly
            100                 105                 110

Gln Gly Ser Leu Val Thr Val Ser Ser
            115                 120

<210> SEQ ID NO 100
<211> LENGTH: 108
<212> TYPE: PRT
<213> ORGANISM: Artificial Sequence
<220> FEATURE:
<223> OTHER INFORMATION: CCMB61 VL

<400> SEQUENCE: 100

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Val
                20                  25                  30

Ser Trp Tyr Gln Gln Lys Pro Gly Gln Ala Pro Thr Leu Val Ile Tyr
            35                  40                  45

Gly Lys Asn Asn Arg Pro Ser Gly Ile Pro Asp Arg Phe Ser Gly Ser
    50                  55                  60

Ser Ser Gly Asn Thr Pro Ser Leu Thr Ile Thr Gly Ala Gln Ala Glu
65                  70                  75                  80

Asp Glu Ala Asp Tyr Tyr Cys Asn Ser Arg Asp Ser Ser Asn His Leu
                85                  90                  95

Val Val Phe Gly Gly Arg Thr Lys Leu Thr Val Leu
            100                 105

<210> SEQ ID NO 101
<211> LENGTH: 121
<212> TYPE: PRT
<213> ORGANISM: Artificial Sequence
<220> FEATURE:
<223> OTHER INFORMATION: CCMB66 VH

<400> SEQUENCE: 101

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Pro Ala Pro Thr Val Asn Asp Leu Asp Tyr Trp Gly
                100                 105                 110

Gln Gly Thr Leu Val Thr Val Ser Ser
        115                 120

<210> SEQ ID NO 102
<211> LENGTH: 107
<212> TYPE: PRT
<213> ORGANISM: Artificial Sequence
<220> FEATURE:
<223> OTHER INFORMATION: CCMB66 VL

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Tyr Ser Thr Pro Leu
                85                  90                  95
Thr Phe Gly Gln Gly Thr Lys Val Glu Ile Lys
            100                 105
```

ANTI-CEACAM ANTIBODIES AND USES THEREOF

CROSS REFERENCE TO RELATED APPLICATIONS

This application claims priority to U.S. Provisional Application Ser. No. 62/907,224, filed 27 Sep. 2019. The disclosure of the aforementioned application is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "JBI6156USNP1_sequence_listing.txt" and a creation date of Aug. 29, 2020 and having a size of 62 kb. The sequence listing submitted via EFS-Web is part of the specification and is herein incorporated by reference in its entirety.

FIELD OF THE INVENTION

The disclosure provided herein relates to antibodies specific to CEACAM1, and, optionally, CEACAM5 and/or CEACAM6, and methods of producing and using the described antibodies.

BACKGROUND OF THE INVENTION

The ability of the immune system to control infections or tumors is often subverted by host mechanisms designed to keep the immune system in check. These immune checkpoints can prevent immune activation even under appropriate circumstances. As many immune checkpoints have evolved to protect healthy tissues and cells, pathogens and tumors have adapted the ability to use these mechanisms to their advantage. Blocking of these immune checkpoints has become a successful strategy in oncology therapeutics and has promoted deeper understanding of immune control mechanisms that may help tumors avoid immune control.

Therapeutics targeting CTLA-4 and PD-1 have taken advantage of this by blocking receptors on the T cells responsible for inducing tumor cell death. Tumor expressing the ligands for PD-1 and CTLA-4 can no longer inhibit the immune responses of these T cells and are then cleared by the immune response. This novel mechanism of immune checkpoint inhibition has led to significant improvement in disease outcomes, but only works in a relatively small proportion of patients.

The CEACAM family are highly conserved glycoproteins of the Ig superfamily, that disrupt activation of immune cells. The canonical family member CEACAM1 is overexpressed in multiple cancer types and is unregulated by T cells upon immune activation[12]. Disruption of the CEACAM1 signaling can increase the activity of T cell, releasing them to kill tumor targets. The number CEACAM family members shows that it is an evolutionarily conserved mechanism of immune suppression, with wider impact than something such a PD-1 or CTLA-4. For this reason, targeting CEACAM may be more desirable than other immune checkpoints.

CEACAM1 can be ligated by itself as well as other members of the CEACAM family such as CEACAM5, CEACAM6, and CEACAM8. Current technologies targeting CEACAM1 alone may only prevent T cell subversion by tumors overexpressing CEACAM1 but would less adequately unmask tumors expressing other CEACAM family members, potentially resulting in less potent blocking of immune suppression and ultimately less effective cancer therapy.

Therefore, there is a need to develop additional therapeutics targeting several CEACAM family members.

SUMMARY OF THE INVENTION

The invention provides antibodies binding to CEACAM1, and/or CEACAM5, and/or CEACAM6 thereby improving T cell mediated control of tumor growth. The antibodies of the invention bind either infected or tumor target cells that would otherwise avoid clearance by host immune surveillance. These antibodies also bind immune cells such as T cells, NK cells, or macrophages that are activated in the presence of tumors or infected cells. Such binding prevents inactivation of such immune cells by CEACAM expressing targets.

As multiple CEACAM family members can ligate in cis or trans and down modulate immune responses, the antibodies of the current invention bind and block multiple CEACAM family members. As evolution of the CEACAM family has led to redundant yet genetically and mechanistically similar molecules for immune control, a functional therapeutic must cross-react with these multiple molecules. This multi-specific approach may lead to more potent blocking of immune suppression and a broader functional range than current technology binding a single CEACAM family member.

In one embodiment, the invention relates to an isolated anti-CEACAM (Carcinoembryonic antigen-related cell adhesion molecule) antibody or an antigen-binding fragment thereof, comprising a HCDR1, a HCDR2, a HCDR3, a LCDR1, a LCDR2 and a LCDR3 of SEQ ID NOs: 7, 8, 9, 10, 11, and 12, respectively. In another embodiment, the isolated anti-CEACAM antibody or an antigen-binding fragment thereof, comprises a heavy chain variable region (VH) of SEQ ID NO: 79 and a light chain variable region (VL) of SEQ ID NO: 80.

In another embodiment, an isolated anti-CEACAM antibody or an antigen-binding fragment thereof, comprises a HCDR1, a HCDR2, a HCDR3, a LCDR1, a LCDR2 and a LCDR3 of SEQ ID NOs: 13, 14, 15, 16, 17, and 18, respectively. In another embodiment, the isolated anti-CEACAM antibody or an antigen-binding fragment thereof, comprises VH of SEQ ID NO: 81 and a VL of SEQ ID NO: 82.

In another embodiment, an isolated anti-CEACAM antibody or an antigen-binding fragment thereof, comprises a HCDR1, a HCDR2, a HCDR3, a LCDR1, a LCDR2 and a LCDR3 of SEQ ID NOs: 19, 20, 21, 22, 23, and 24, respectively. In another embodiment, the isolated anti-CEACAM antibody or an antigen-binding fragment thereof of claim 5, comprises a VH of SEQ ID NO: 83 and a VL of SEQ ID NO: 84.

In another embodiment, an isolated anti-CEACAM antibody or an antigen-binding fragment thereof, comprises a HCDR1, a HCDR2, a HCDR3, a LCDR1, a LCDR2 and a LCDR3 of SEQ ID NOs: 25, 26, 27, 28, 29, and 30, respectively. In another embodiment, the isolated anti-CEACAM antibody or an antigen-binding fragment thereof of claim 7, comprises a VH of SEQ ID NO: 85 and a VL of SEQ ID NO: 86.

In another embodiment, an isolated anti-CEACAM antibody or an antigen-binding fragment thereof, comprises a HCDR1, a HCDR2, a HCDR3, a LCDR1, a LCDR2 and a LCDR3 of SEQ ID NOs: 31, 32, 33, 34, 35, and 36, respectively. In another embodiment, the isolated anti-CEACAM antibody or an antigen-binding fragment thereof of claim 9, comprises a VH of SEQ ID NO: 87 and a VL of SEQ ID NO: 88.

In another embodiment, an isolated anti-CEACAM antibody or an antigen-binding fragment thereof, comprises a HCDR1, a HCDR2, a HCDR3, a LCDR1, a LCDR2 and a LCDR3 of SEQ ID NOs: 37, 38, 39, 40, 41, and 42, respectively. In another embodiment, the isolated anti-CEACAM antibody or an antigen-binding fragment thereof of claim 11, comprises a VH of SEQ ID NO: 89 and a VL of SEQ ID NO: 90.

In another embodiment, an isolated anti-CEACAM antibody or an antigen-binding fragment thereof, comprising a HCDR1, a HCDR2, a HCDR3, a LCDR1, a LCDR2 and a LCDR3 of SEQ ID NOs: 43, 44, 45, 46, 47, and 48, respectively. In another embodiment, the isolated anti-CEACAM antibody or an antigen-binding fragment thereof of claim 13, comprises a VH of SEQ ID NO: 91 and a VL of SEQ ID NO: 92.

In another embodiment, an isolated anti-CEACAM antibody or an antigen-binding fragment thereof, comprises a HCDR1, a HCDR2, a HCDR3, a LCDR1, a LCDR2 and a LCDR3 of SEQ ID NOs: 49, 50, 51, 52, 53, and 54, respectively. In another embodiment, the isolated anti-CEACAM antibody or an antigen-binding fragment thereof of claim 15, comprises a VH of SEQ ID NO: 93 and a VL of SEQ ID NO: 94.

In another embodiment, an isolated anti-CEACAM antibody or an antigen-binding fragment thereof, comprises a HCDR1, a HCDR2, a HCDR3, a LCDR1, a LCDR2 and a LCDR3 of SEQ ID NOs: 55, 56, 57, 58, 59, and 60, respectively. In another embodiment, the isolated anti-CEACAM antibody or an antigen-binding fragment thereof of claim 17, comprises a VH of SEQ ID NO: 95 and a VL of SEQ ID NO: 96.

In another embodiment, an isolated anti-CEACAM antibody or an antigen-binding fragment thereof, comprises a HCDR1, a HCDR2, a HCDR3, a LCDR1, a LCDR2 and a LCDR3 of SEQ ID NOs: 61, 62, 63, 64, 65, and 66, respectively. In another embodiment, the isolated anti-CEACAM antibody or an antigen-binding fragment thereof of claim 19, comprises a VH of SEQ ID NO: 97 and a VL of SEQ ID NO: 98.

In another embodiment, an isolated anti-CEACAM antibody or an antigen-binding fragment thereof, comprises a HCDR1, a HCDR2, a HCDR3, a LCDR1, a LCDR2 and a LCDR3 of SEQ ID NOs: 67, 68, 69, 70, 71, and 72, respectively. In another embodiment, the isolated anti-CEACAM antibody or an antigen-binding fragment thereof of claim 21, comprises a VH of SEQ ID NO: 99 and a VL of SEQ ID NO: 100.

In another embodiment, an isolated anti-CEACAM antibody or an antigen-binding fragment thereof, comprises a HCDR1, a HCDR2, a HCDR3, a LCDR1, a LCDR2 and a LCDR3 of SEQ ID NOs: 73, 74, 75, 76, 77, and 78, respectively. In another embodiment, the isolated anti-CEACAM antibody or an antigen-binding fragment thereof of claim 23, comprises a VH of SEQ ID NO: 101 and a VL of SEQ ID NO: 102.

In another embodiment, the invention relates to an isolated anti-CEACAM antibody or the antigen binding fragment thereof, wherein the antibody or the antigen binding fragment thereof that competes for binding to CEACAM1, and optionally CEACAM5 or CEACAM6, with a reference antibody comprising
  a heavy chain variable region (VH) of SEQ ID NO: 79 and a light chain variable region (VL) of SEQ ID NO: 80; or
  a VH of SEQ ID NO: 81 and the VL of SEQ ID NO: 82;
  a VH of SEQ ID NO: 83 and the VL of SEQ ID NO: 84;
  a VH of SEQ ID NO: 85 and the VL of SEQ ID NO: 86;
  a VH of SEQ ID NO: 87 and the VL of SEQ ID NO: 88;
  a VH of SEQ ID NO: 89 and the VL of SEQ ID NO: 90;
  a VH of SEQ ID NO: 91 and the VL of SEQ ID NO: 92;
  a VH of SEQ ID NO: 93 and the VL of SEQ ID NO: 94;
  a VH of SEQ ID NO: 95 and the VL of SEQ ID NO: 96;
  a VH of SEQ ID NO: 97 and the VL of SEQ ID NO: 98;
  a VH of SEQ ID NO: 99 and the VL of SEQ ID NO: 100; or
  a VH of SEQ ID NO: 101 and the VL of SEQ ID NO: 102.

In another embodiment, the isolated anti-CEACAM antibody or the antigen binding fragment thereof is an IgG1, an IgG2, an IgG3 or an IgG4 isotype.

In another embodiment, the isolated anti-CEACAM antibody is a multispecific antibody.

In another embodiment, the isolated anti-CEACAM antibody is a bispecific antibody.

In another embodiment, a pharmaceutical composition comprises the anti-CEACAM antibody or the antigen-binding fragment thereof and a pharmaceutically acceptable carrier.

In another embodiment, the isolated anti-CEACAM antibody or the antigen-binding fragment thereof is conjugated to one or more heterologous molecules.

In another embodiment, the invention relates to an isolated polynucleotide encoding the anti-CEACAM antibody or the antigen binding fragment.

In another embodiment, the invention relates to an isolated polynucleotide encoding the anti-CEACAM antibody or the antigen binding fragment thereof and comprising a polynucleotide sequence encoding a sequence selected from the group consisting of SEQ ID NOs: 79-102.

In another embodiment, the invention relates to a vector comprising the polynucleotide comprising a polynucleotide sequence encoding a sequence selected from the group consisting of SEQ ID NOs: 79-102. In another embodiment, the invention relates to a host cell comprising the vector.

In another embodiment, the invention relates to a method of producing the anti-CEACAM antibody or the antigen binding fragment thereof, comprising culturing the host cell in conditions that the antibody is expressed, and recovering the antibody produced by the host cell.

In another embodiment, the invention relates to a method of treating a CEACAM positive cancer in a subject in need thereof, comprising administering a therapeutically effective amount of the isolated anti-CEACAM antibody of the invention or the antigen binding fragment thereof or the pharmaceutical composition of the invention to the subject to treat the CEACAM positive cancer. In another embodiment, the method wherein the anti-CEACAM antibody or the antigen binding fragment thereof is administered in combination with a second therapeutic agent. In another embodiment, the method is when the second therapeutic agent is surgery, chemotherapy, androgen deprivation therapy or radiation, or any combination thereof In another embodiment, the invention relates to a kit comprising the antibody of the invention.

Figure 1:
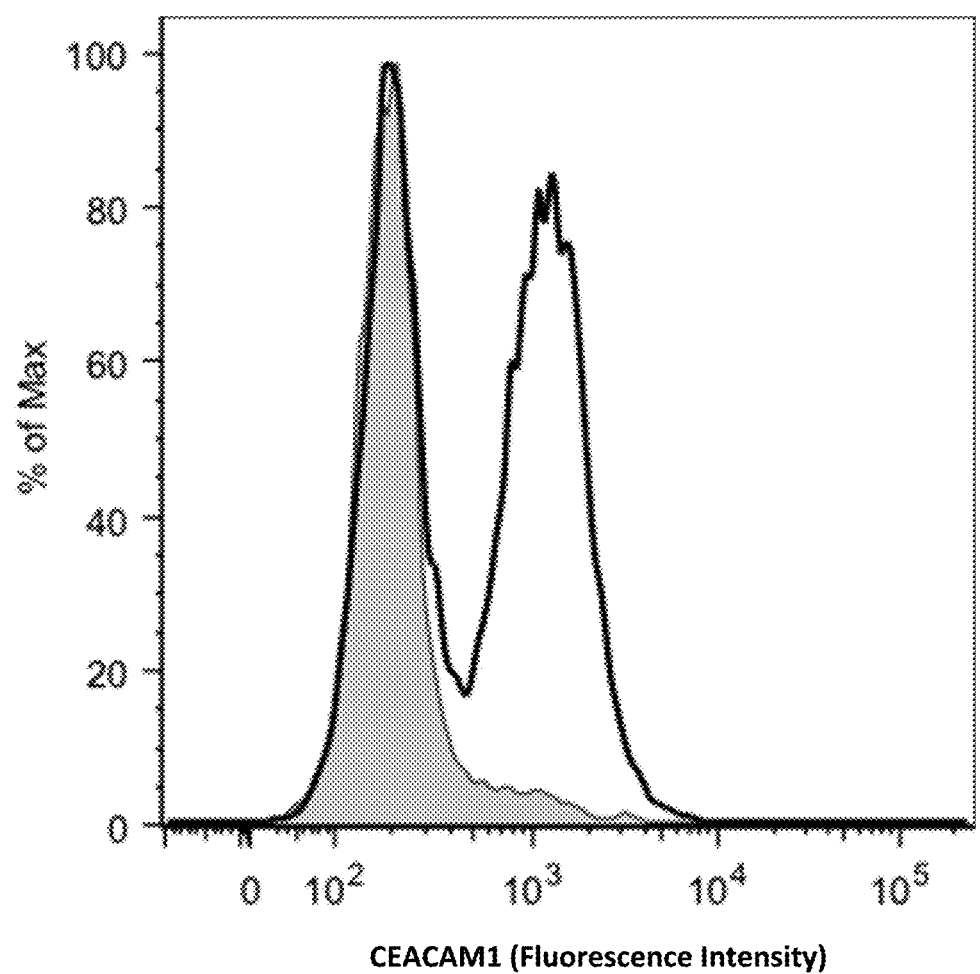
FIG. 1 illustrates a representative flow cytometry graph; black line shows expression of CEACAM1 on anti-CD3 activated T cells, grey line shows baseline CEACAM expression on resting T cells prior to activation.
Figure 2:
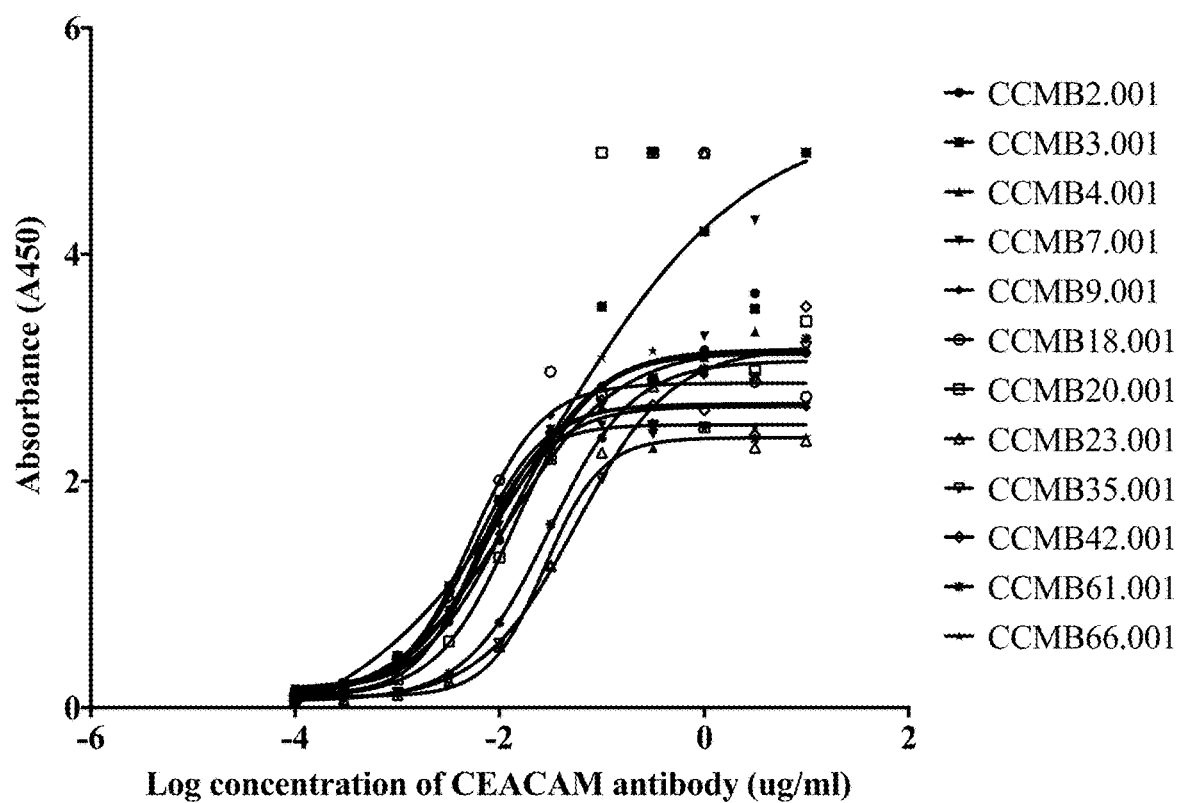

FIG. 2 illustrates the binding of CEACAM antibodies to recombinant CEACAM 1.

Figure 3:
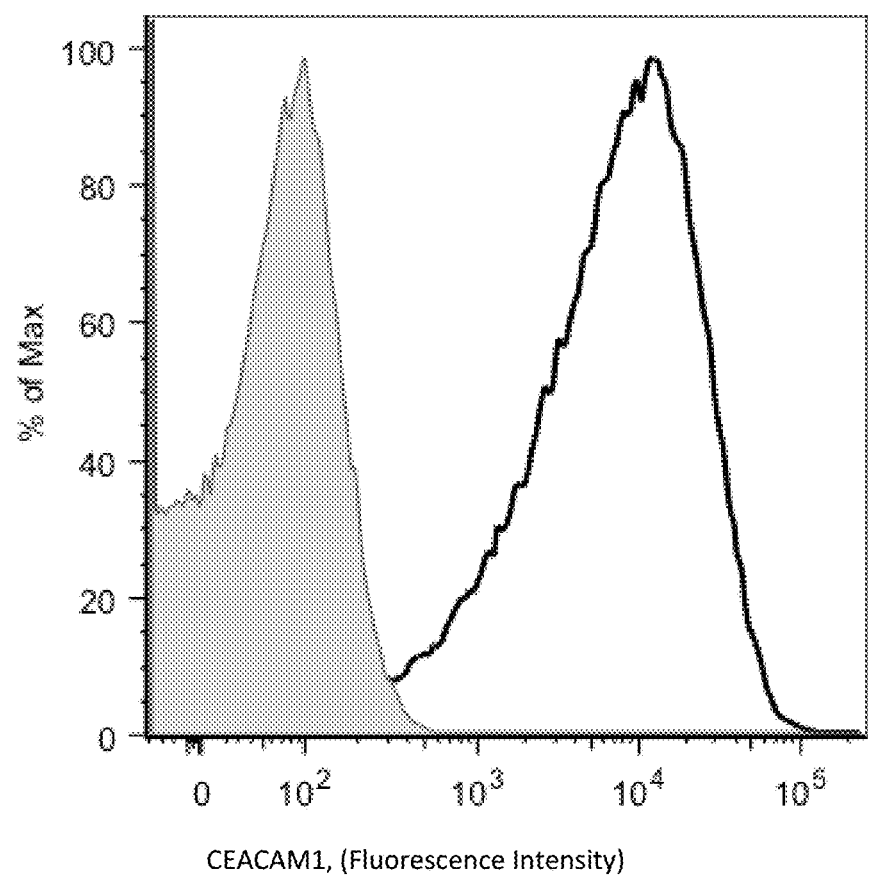

FIG. 3 illustrates a representative flow cytometry graph; black line shows HEK293T cells transfected to overexpress CEACAM1, grey line shows parental HEK293T cells that were not expressing CEACAM1.

Figure 4:
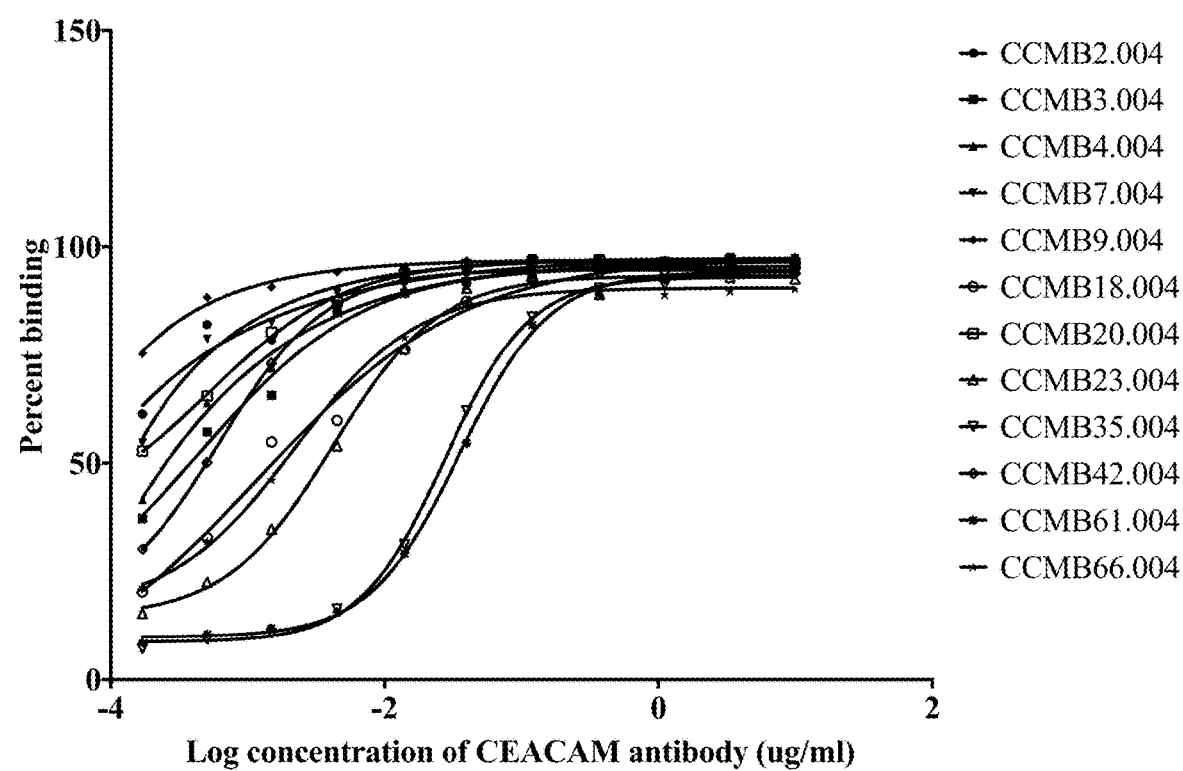
Figure 5A:
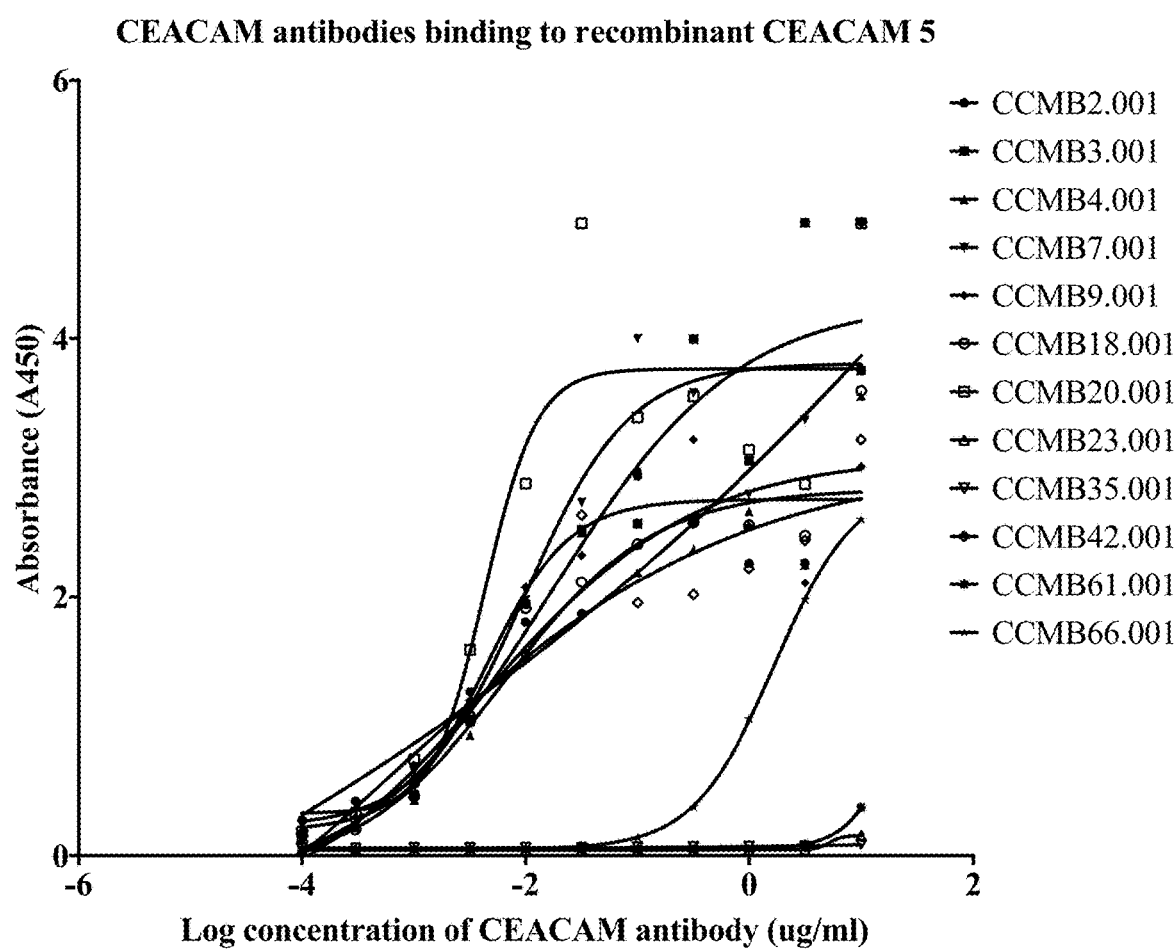

FIG. 4 illustrate the binding curves for anti-CEACAM1 antibodies to HEK293T cells overexpressing CEACAM1, by flow cytometry FIG. 5a illustrates the binding of anti-CEACAM1 antibodies to immobilized recombinant CEACAM5 by ELISA.

Figure 5B:
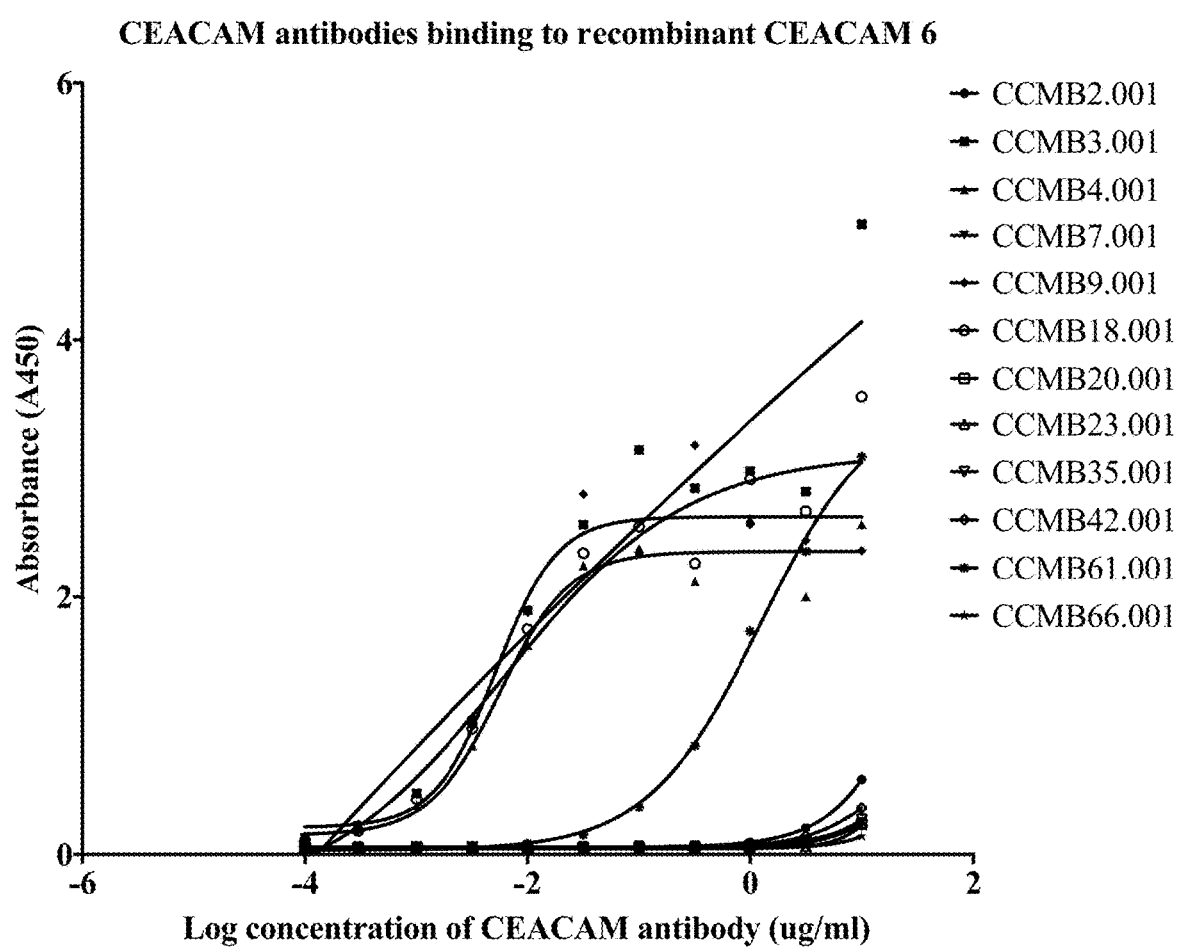

FIG. 5b illustrates the binding of anti-CEACAM1 antibodies to immobilized recombinant CEACAM6 by ELISA.

Figure 6A:
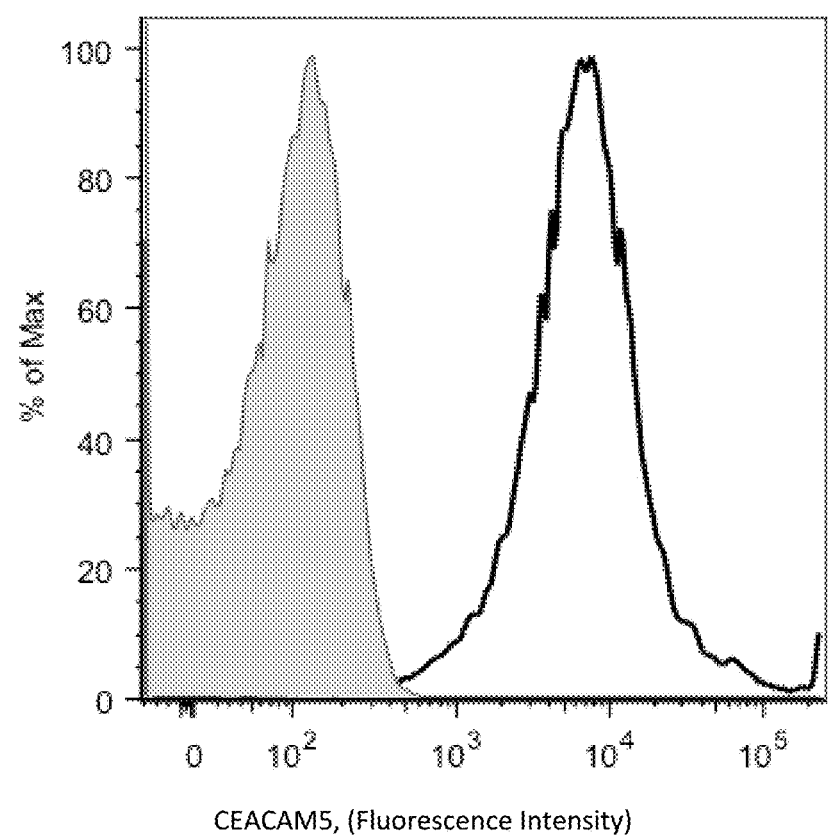

FIG. 6a illustrates a representative flow cytometry graph; black line shows HEK293T cells overexpressing CEACAM5, grey line shows cells that were not expressing CEACAM5.

Figure 6B:
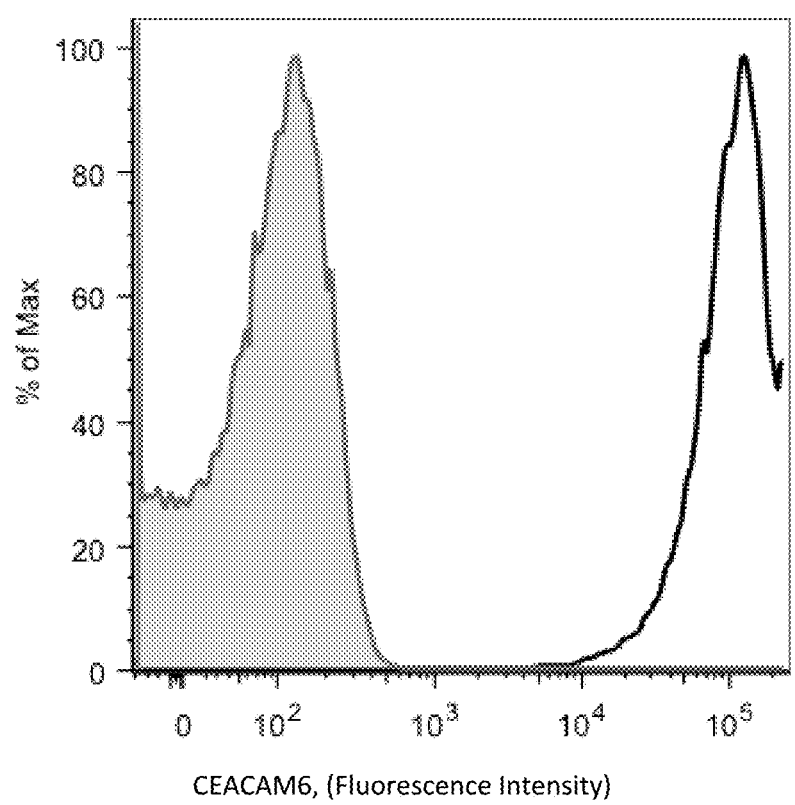

FIG. 6b illustrates a representative flow cytometry graph; black line shows HEK293T cells overexpressing CEACAM6, grey line shows parental HEK293T cells that were not expressing CEACAM6.

Figure 7A:
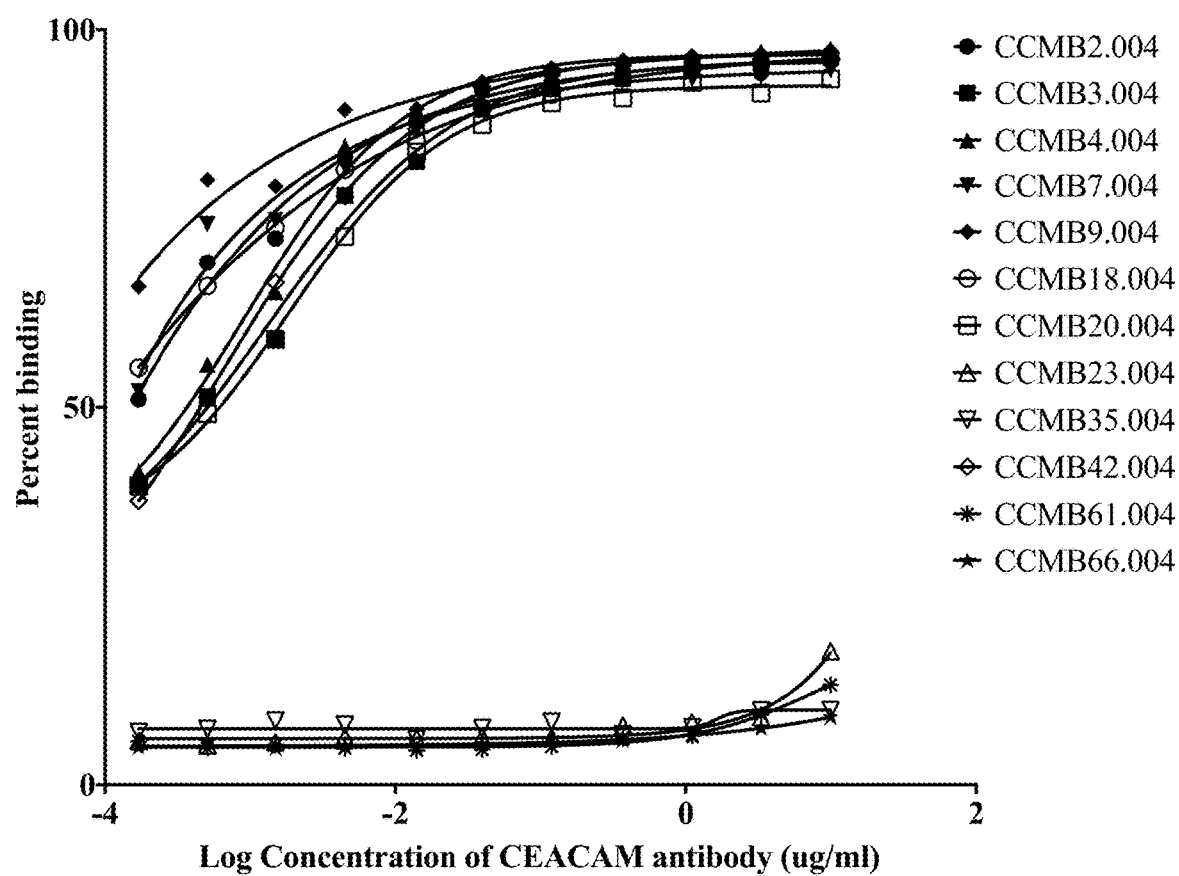

FIG. 7a. illustrates the binding of anti-CEACAM1 antibodies to CEACAM5 overexpressing HEK293T cells.

Figure 7B:
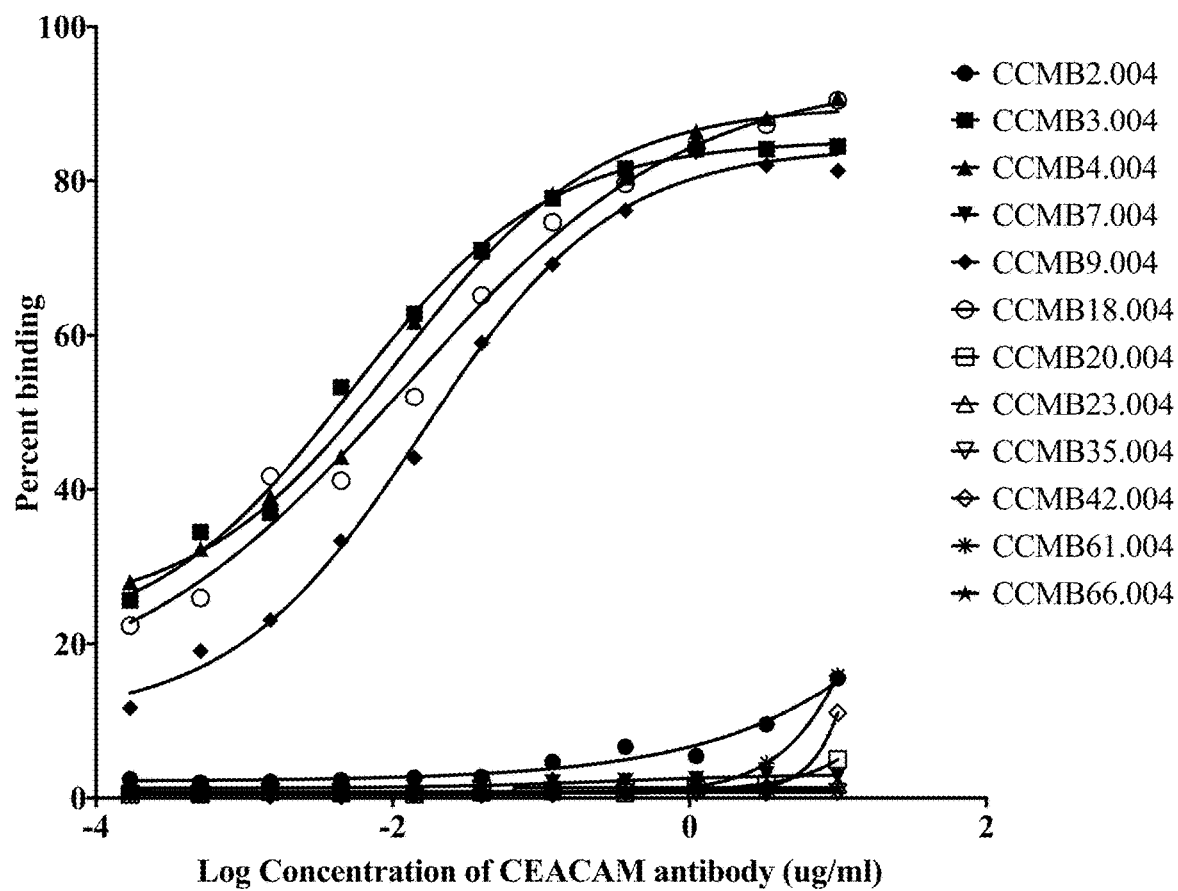

FIG. 7b. illustrates the binding of anti-CEACAM1 antibodies to CEACAM6 overexpressing HEK293T cells.

Figure 8:
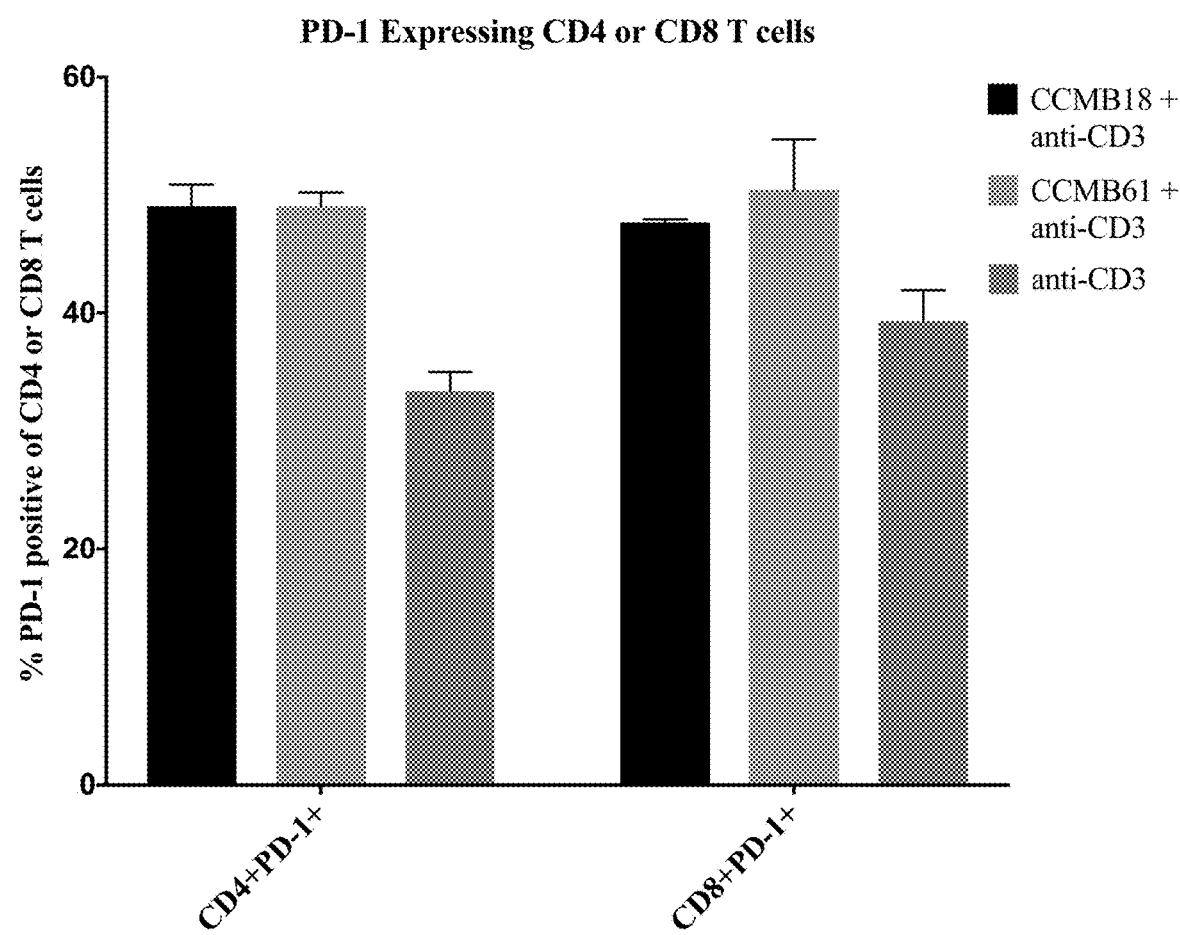

FIG. 8 illustrates the percent of PD-1 positive T cells (either CD4+ or CD8+) upon stimulation by either anti-CD3 antibody (dark grey), or combination of the anti-CD3 antibody and anti-CEACAM antibody CCMB18 (black), or combination of the anti-CD3 antibody and anti-CEACAM antibody CCMB61 (light grey).

Figure 9:
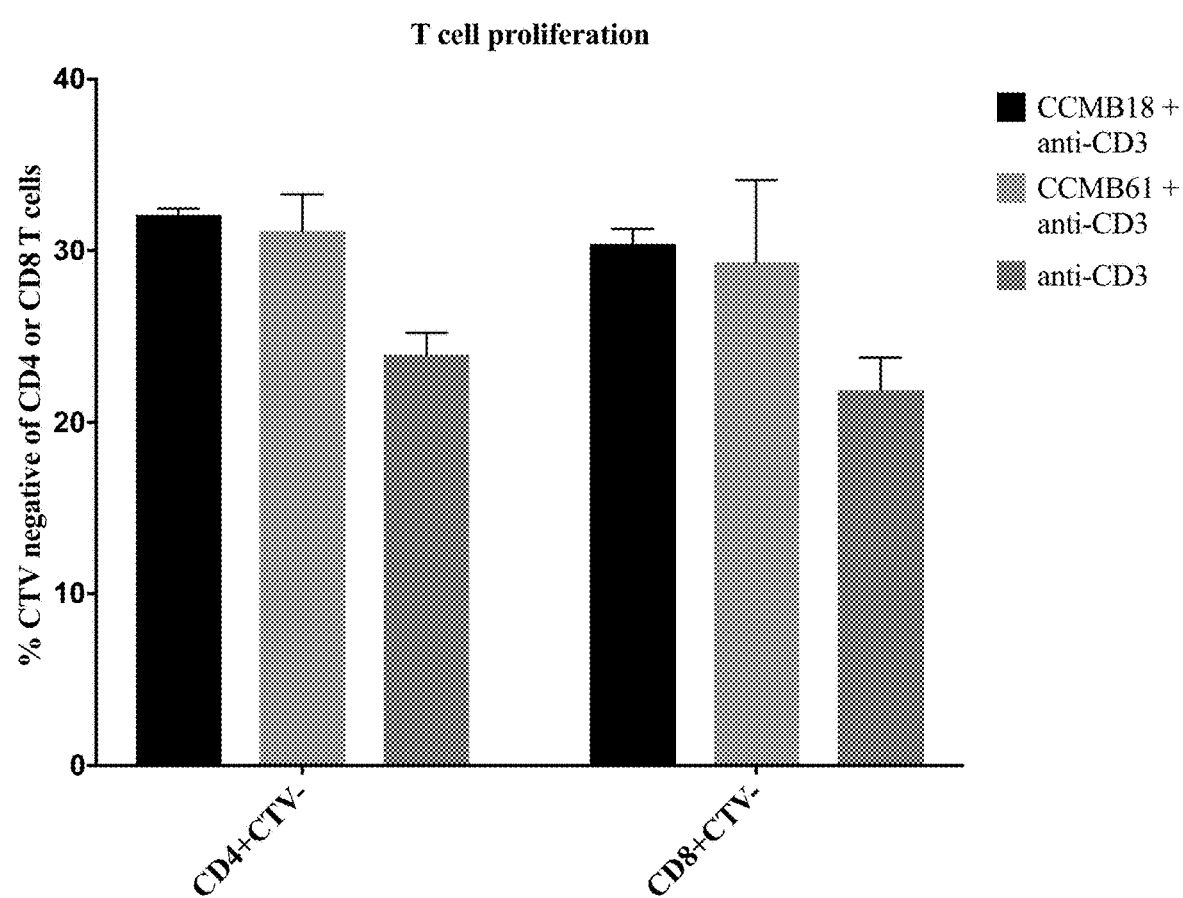

FIG. 9 illustrates the percent of Cell Trace Violet-negative T cells (either CD4+ or CD8+) upon stimulation by either anti-CD3 antibody (dark grey), or combination of the anti-CD3 antibody and anti-CEACAM antibody CCMB18 (black), or combination of the anti-CD3 antibody and anti-CEACAM antibody CCMB61 (light grey).

Figure 10A:
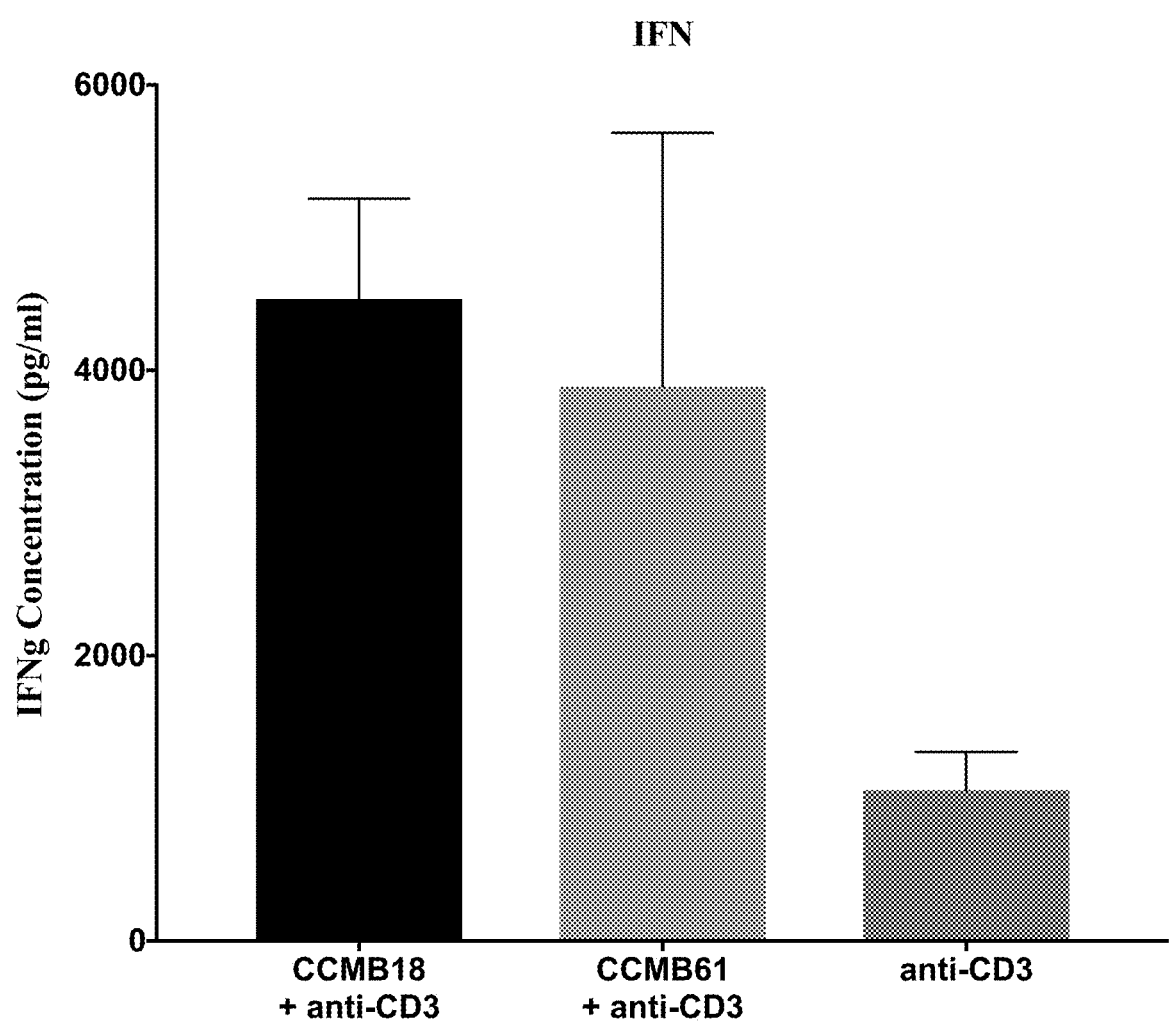

FIG. 10a illustrates the secretion of interferon (IFN) gamma from T cells stimulated with anti-CD3 antibody in the presence or absence of anti-CEACAM binding antibodies (CCMB18 or CCMB61).

Figure 10B:
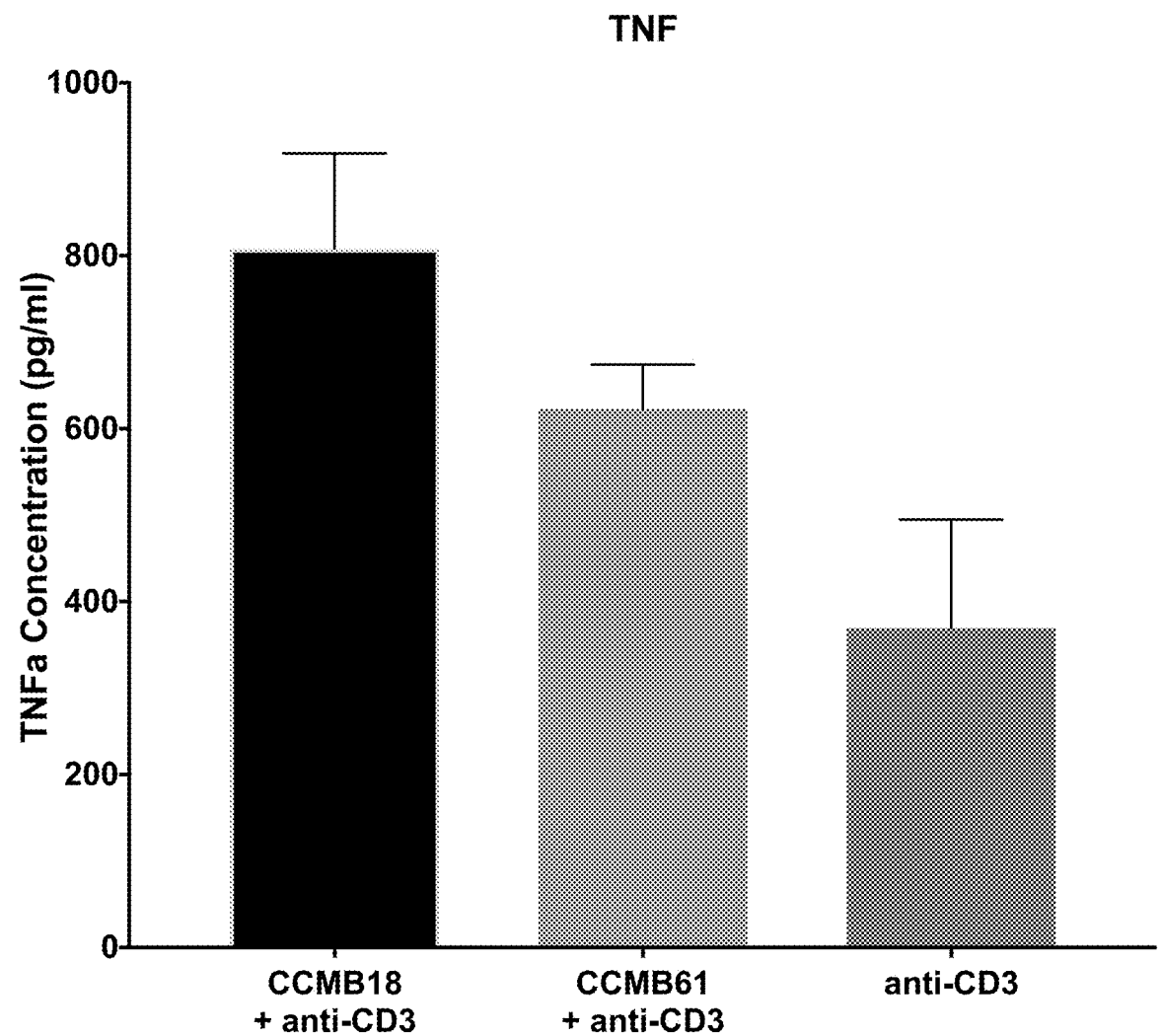

FIG. 10b illustrates the secretion of tumor necrosis factor (TNF) alpha from T cells stimulated with anti-CD3 antibody in the presence or absence of anti-CEACAM binding antibodies (CCMB18 or CCMB61).

DETAILED DESCRIPTION OF THE INVENTION

All publications, including but not limited to patents and patent applications, cited in this specification are herein incorporated by reference as though fully set forth.

The disclosed subject matter may be understood more readily by reference to the following detailed description taken in connection with the accompanying figures, which form a part of this disclosure. It is to be understood that the disclosed subject matter is not limited to those described and/or shown herein, and that the terminology used herein is for the purpose of describing particular embodiments by way of example only and is not intended to be limiting of the claimed subject matter.

Unless specifically stated otherwise, any description as to a possible mechanism or mode of action or reason for improvement is meant to be illustrative only, and the disclosed subject matter are not to be constrained by the correctness or incorrectness of any such suggested mechanism or mode of action or reason for improvement.

When a range of values is expressed, another embodiment includes from the one particular value and/or to the other particular value. Further, reference to values stated in ranges include each and every value within that range. All ranges are inclusive and may be combined. When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed subject matter which are, for clarity, described herein in the context of separate embodiments, may also be provided in combination in a single embodiment. Conversely, various features of the disclosed subject matter that are, for brevity, described in the context of a single embodiment, may also be provided separately or in any subcombination.

Definitions

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "about" when used in reference to numerical ranges, cutoffs, or specific values is used to indicate that the recited values may vary by up to as much as 10% from the listed value. Thus, the term "about" is used to encompass variations of ±10% or less, variations of ±5% or less, variations of ±1% or less, variations of ±0.5% or less, or variations of ±0.1% or less from the specified value.

"Antibodies" is meant in a broad sense and includes immunoglobulin molecules including monoclonal antibodies including murine, human, humanized and chimeric monoclonal antibodies, antigen binding fragments, multi-specific antibodies, such as bispecific, trispecific, tetraspecific etc., dimeric, tetrameric or multimeric antibodies, single chain antibodies, domain antibodies and any other modified configuration of the immunoglobulin molecule that comprises an antigen binding site of the required specificity. "Full length antibodies" are comprised of two heavy chains (HC) and two light chains (LC) inter-connected by disulfide bonds as well as multimers thereof (e.g. IgM). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4.

"Complementarity determining regions (CDR)" are antibody regions that bind an antigen. CDRs may be defined using various delineations such as Kabat (Wu et al. (1970) *J Exp Med* 132: 211-50) (Kabat et al., Sequences of Proteins of Immunological Interest, 5th Ed. Public Health Service, National Institutes of Health, Bethesda, Md., 1991), Chothia (Chothia et al. (1987) *J Mol Bio* 1196: 901-17), IMGT (Lefranc et al. (2003) *Dev Comp Immunol* 27: 55-77) and AbM (Martin and Thornton (1996) *J Bmol Biol* 263: 800-

15). The correspondence between the various delineations and variable region numbering are described (see e.g. Lefranc et al. (2003 *Dev Comp Immunol* 27: 55-77; Honegger and Pluckthun, (2001) *J Mol Biol* 309:657-70; International ImMunoGeneTics (IMGT) database; Web resources, http://www_imgt_org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification.

Immunoglobulins can be assigned to five major classes, IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species can be assigned to one of two clearly distinct types, namely kappa (κ) and lambda (λ), based on the amino acid sequences of their constant domains.

"Antigen binding fragment" refers to a portion of an immunoglobulin molecule that binds an antigen. Antigen binding fragments may be synthetic, enzymatically obtainable or genetically engineered polypeptides and include the VH, the VL, the VH and the VL, Fab, F(ab')2, Fd and Fv fragments, domain antibodies (dAb) consisting of one VH domain or one VL domain, shark variable IgNAR domains, camelized VH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3. VH and VL domains may be linked together via a synthetic linker to form various types of single chain antibody designs where the VH/VL domains may pair intramolecularly, or intermolecularly in those cases when the VH and VL domains are expressed by separate single chain antibody constructs, to form a monovalent antigen binding site, such as single chain Fv (scFv) or diabody; described for example in Int. Patent Publ. Nos. WO1998/44001, WO1988/01649, WO1994/13804 and WO1992/01047.

An antibody variable region consists of a "framework" region interrupted by three "antigen binding sites". The antigen binding sites are defined using various terms: (i) Complementarity Determining Regions (CDRs), three in the VH (HCDR1, HCDR2, HCDR3) and three in the VL (LCDR1, LCDR2, LCDR3) are based on sequence variability (Wu and Kabat, J Exp Med 132:211-50, 1970; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia and Lesk, Mol Biol 196:901-17, 1987). Other terms include "IMGT-CDRs" (Lefranc et al., Dev Comparat Immunol 27:55-77, 2003) and "Specificity Determining Residue Usage" (SDRU) (Almagro, Mol Recognit 17:132-43, 2004). The International ImMunoGeneTics (IMGT) database (http://www_imgt_org) provides a standardized numbering and definition of antigen-binding sites. The correspondence between CDRs, HVs and IMGT delineations is described in Lefranc et al., Dev Comparat Immunol 27:55-77, 2003.

"Antibody fragments" refers to a portion of an immunoglobulin molecule that retains the heavy chain and/or the light chain antigen binding site, such as heavy chain complementarity determining regions (HCDR) 1, 2 and 3, light chain complementarity determining regions (LCDR) 1, 2 and 3, a heavy chain variable region (VH), or a light chain variable region (VL). Antibody fragments include well known Fab, F(ab')2, Fd and Fv fragments as well as domain antibodies (dAb) consisting one VH domain. VH and VL domains may be linked together via a synthetic linker to form various types of single chain antibody designs where the VH/VL domains pair intramolecularly, or intermolecularly in those cases when the VH and VL domains are expressed by separate single chain antibody constructs, to form a monovalent antigen binding site, such as single chain Fv (scFv) or diabody; described for example in Int. Pat. Publ. No. WO1998/44001, Int. Pat. Publ. No. WO1988/01649; Int. Pat. Publ. No. WO1994/13804; Int. Pat. Publ. No. WO1992/01047.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. A bispecific monoclonal antibody binds two distinct antigenic epitopes. Monoclonal antibodies may have heterogeneous glycosylation within the antibody population. Monoclonal antibody may be monospecific or multispecific such as bispecific, monovalent, bivalent or multivalent.

"Chimeric antibodies" are molecules, the different portions of which are derived from different animal species, such as those having a variable region derived from a murine mAb and a human immunoglobulin constant region. Antibodies which have variable region framework residues substantially from human antibody (termed an acceptor antibody) and complementarity determining regions substantially from a mouse antibody (termed a donor antibody) are also referred to as humanized antibodies. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (e.g. PCT patent applications WO 86/01533, WO 97/02671 and WO 90/07861, and U.S. Pat. Nos. 5,693,762, 5,693,761, and 5,225,539). Additionally, CDR grafting may be performed to alter certain properties of the antibody molecule including affinity or specificity. A non-limiting example of CDR grafting is disclosed in U.S. Pat. No. 5,225,539.

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) J Mol Biol 296:57-86, or synthetic HCDR3 incorporated into human immunoglobulin gene libraries displayed on phage, for example as described in Shi et al., (2010) J Mol Biol 397:385-96, and in Int. Patent Publ. No. WO2009/085462.

"Bispecific" refers to an antibody that specifically binds two distinct antigens or two distinct epitopes within the same antigen. The bispecific antibody may have cross-reactivity to other related antigens, for example to the same antigen from other species (homologs), such as human or monkey, for example *Macaca cynomolgus* (cynomolgus, cyno) or *Pan troglodytes*, or may bind an epitope that is shared between two or more distinct antigens.

"Multispecific" refers to an antibody that specifically binds two or more distinct antigens or two or more distinct epitopes within the same antigen. The multispecific antibody may have cross-reactivity to other related antigens, for example to the same antigen from other species (homologs), such as human or monkey, for example *Macaca cynomolgus* (cynomolgus, cyno) or Pan troglodytes, or may bind an epitope that is shared between two or more distinct antigens.

"Epitope" refers to a portion of an antigen to which an antibody specifically binds. Epitopes typically consist of chemically active (such as polar, non-polar or hydrophobic) surface groupings of moieties such as amino acids or polysaccharide side chains and may have specific three-dimensional structural characteristics, as well as specific charge characteristics. An epitope may be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Effective amount" refers to an amount effective, at dosages and for periods of time necessary, to achieve a desired result. An effective amount may vary according to factors such as the disease state, age, sex, and weight of the individual, and the ability of the antibody to elicit a desired response in the individual. An effective amount is also one in which any toxic or detrimental effects of the agent are outweighed by the beneficial effects.

A "isolated cell or tissue sample" is a collection of cells obtained from a tissue of a subject or individual. The source of the cells or tissue sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The cells or tissue sample may also be primary or cultured cells or cell lines. Optionally, the tissue sample or tissue fragments is obtained from a disease tissue/organ. The tissue sample may contain compounds which are not naturally intermixed with the tissue in nature such as preservatives, anticoagulants, buffers, fixatives, nutrients, antibiotics, or the like.

"Isolated" refers to a homogenous population of molecules (such as synthetic polynucleotides or a protein such as an antibody) which have been substantially separated and/or purified away from other components of the system the molecules are produced in, such as a recombinant cell, as well as a protein that has been subjected to at least one purification or isolation step. "Isolated antibody" refers to an antibody that is substantially free of other cellular material and/or chemicals and encompasses antibodies that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Recombinant" refers to DNA, antibodies and other proteins that are prepared, expressed, created or isolated by recombinant means when segments from different sources are joined to produce recombinant DNA, antibodies or proteins.

As used herein, an antibody that "specifically binds", or "antigen specific", or "specific for" an antigen target, or is "immunoreactive" with an antigen refers to an antibody or polypeptide binding agent of the invention that binds an antigen with greater affinity than other antigens of similar sequence. In one aspect, the polypeptide binding agents of the invention, or fragments, variants, or derivatives thereof, will bind with a greater affinity to human antigen as compared to its binding affinity to similar antigens of other, i.e., non-human, species, but polypeptide binding agents that recognize and bind orthologs of the target are within the scope of the invention.

"Subject" refers to human and non-human animals, including all vertebrates, e.g., mammals and non-mammals, such as non-human primates, mice, rabbits, sheep, dogs, cats, horses, cows, chickens, amphibians, and reptiles. In many embodiments of the described subject matter, the subject is a human.

"Treating" or "treatment" refer to any success or indicia of success in the attenuation or amelioration of an injury, pathology, or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters, including the results of a physical examination, neurological examination, or psychiatric evaluations.

"Variant" refers to a polypeptide or a polynucleotide that differs from a reference polypeptide or a reference polynucleotide by one or more modifications, for example one or more substitutions, insertions or deletions.

"Vector" refers to a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system, such as a cell, virus, animal, plant, and reconstituted biological systems utilizing biological components capable of duplicating a vector. The vector polynucleotide may be DNA or RNA molecules or a hybrid of these, single stranded or double stranded.

"Expression vector" refers to a vector that can be utilized in a biological system or in a reconstituted biological system to direct the translation of a polypeptide encoded by a polynucleotide sequence present in the expression vector.

"Polynucleotide" refers to a synthetic molecule comprising a chain of nucleotides covalently linked by a sugar-phosphate backbone or other equivalent covalent chemistry. cDNA is an exemplary synthetic polynucleotide.

"Polypeptide" or "protein" refers to a molecule that comprises at least two amino acid residues linked by a peptide bond to form a polypeptide. Small polypeptides of less than 50 amino acids may be referred to as "peptides".

"CEACAM1" (Carcinoembryonic antigen-related cell adhesion molecule 1) refers to the protein product of the CEACAM1 gene, e.g., NP-001020083.1, NP-001703.2. The amino acid sequence of the full length human CEACAM1 is shown in SEQ ID NO: 1. The extracellular domain of CEACAM1 is shown in SEQ ID NO: 2 and spans residues 35-428 of the full length CEACAM1. In humans, 11 different CEACAM1 splice variants are known. Individual CEACAM1 isoforms differ with respect to the number of extracellular immunoglobulin-like domains, or membrane anchorage and/or the length of their cytoplasmic tail. All variants, including these splice variants are included within the term "CEACAM1".

(full length human CEACAM1):
SEQ ID NO: 1
MGHLSAPLHRVRVPWQGLLLLTASLLTFWNPPTTAQLTTESMPFNVA

EGKEVLLLVHNLPQQLFGYSWYKGERVDGNRQIVGYAIGTQQATPG

PANSGRETIYPNASLLIQNVTQNDTGFYTLQVIKSDLVNEEATGQF

HVYPELPKPSISSNNSNPVEDKDAVAFTCEPETQDTTYLWWINNQS

LPVSPRLQLSNGNRTLTLLSVTRNDTGPYECEIQNPVSANRSDPVT

LNVTYGPDTPTISPSDTYYRPGANLSLSCYAASNPPAQYSWLINGT

FQQSTQELFIPNITVNNSGSYTCHANNSVTGCNRTTVKTIIVTELS

PVVAKPQIKASKTTVTGDKDSVNLTCSTNDTGISIRWFFKNQSLPS

SERMKLSQGNTTLSINPVKREDAGTYWCEVFNPISKNQSDPIMLNV

NYNALPQENGLSPGAIAGIVIGVVALVALIAVALACFLHFGKTGRA

SDQRDLTEHKPSVSNHTQDHSNDPPNKMNEVTYSTLNFEAQQPTQP

TSASPSLTATEIIYSEVKKQ (extracellular domain of human CEACAM1):
SEQ ID NO: 2
QLTTESMPFNVAEGKEVLLLVHNLPQQLFGYSWYKGERVDGNRQIV

GYAIGTQQATPGPANSGRETIYPNASLLIQNVTQNDTGFYTLQVIK

SDLVNEEATGQFHVYPELPKPSISSNNSNPVEDKDAVAFTCEPETQ

DTTYLWWINNQSLPVSPRLQLSNGNRTLTLLSVTRNDTGPYECEIQ

NPVSANRSDPVTLNVTYGPDTPTISPSDTYYRPGANLSLSCYAASN

PPAQYSWLINGTFQQSTQELFIPNITVNNSGSYTCHANNSVTGCNR

TTVKTIIVTELSPVVAKPQIKASKTTVTGDKDSVNLTCSTNDTGIS

IRWFFKNQSLPSSERMKLSQGNTTLSINPVKREDAGTYWCEVFNPI

SKNQSDPIMLNVNYNALPQENGLSPG

An "anti-CEACAM1 antibody", "an antibody which recognizes CEACAM1", "an antibody against CEACAM1", or "an antibody to CEACAM1" is an antibody that binds to the CEACAM1 protein with sufficient affinity and specificity. Typically, an antibody according to the present teachings is capable of binding CEACAM1 with a minimal affinity of about $10^{-8}$ or $10^{-9}$ M or more.

"CEACAM5" (Carcinoembryonic antigen-related cell adhesion molecule 5) refers to the protein product of the CEACAM5 gene. The amino acid sequence of the full length human CEACAM5 is shown in SEQ ID NO: 3. Two isoforms produced by alternative splicing have been described in humans to date. All isoforms, including these splice variants are included within the term "CEACAM5".

(full length human CEACAM5):
SEQ ID NO: 3
MESPSAPPHRWCIPWQRLLLLTASLLTFWNPPTTAKLTIESTPFNVAE

GKEVLLLVHNLPQHLFGYSWYKGERVDGNRQIIGYVIGTQQATPGPA

YSGREIIYPNASLLIQNIIQNDTGFYTLHVIKSDLVNEEATGQFRVY

PELPKPSISSNNSKPVEDKDAVAFTCEPETQDATYLWWVNNQSLPVS

PRLQLSNGNRTLTLFNVTRNDTASYKCETQNPVSARRSDSVILNVLY

GPDAPTISPLNTSYRSGENLNLSCHAASNPPAQYSWFVNGTFQQSTQ

ELFIPNITVNNSGSYTCQAHNSDTGLNRTTVTTITVYAEPPKPFITS

NNSNPVEDEDAVALTCEPEIQNTTYLWWVNNQSLPVSPRLQLSNDNR

TLTLLSVTRNDVGPYECGIQNKLSVDHSDPVILNVLYGPDDPTISPS

YTYYRPGVNLSLSCHAASNPPAQYSWLIDGNIQQHTQELFISNITEK

NSGLYTCQANNSASGHSRTTVKTITVSAELPKPSISSNNSKPVEDKD

AVAFTCEPEAQNTTYLWWVNGQSLPVSPRLQLSNGNRTLTLFNVTRN

DARAYVCGIQNSVSANRSDPVTLDVLYGPDTPIISPPDSSYLSGANL

NLSCHSASNPSPQYSWRINGIPQQHTQVLFIAKITPNNNGTYACFVS

NLATGRNNSIVKSITVSASGTSPGLSAGATVGIMIGVLVGVALI

"CEACAM6" (Carcinoembryonic antigen-related cell adhesion molecule 6) refers to the protein product of the CEACAM6 gene. The amino acid sequence of the full length human CEACAM6 is shown in SEQ ID NO: 4.

(full length human CEACAM6):
SEQ ID NO: 4
MGPPSAPPCRLHVPWKEVLLTASLLTFWNPPTTAKLTIESTPFNVAE

GKEVLLLAHNLPQNRIGYSWYKGERVDGNSLIVGYVIGTQQATPGPA

YSGRETIYPNASLLIQNVTQNDTGFYTLQVIKSDLVNEEATGQFHVY

PELPKPSISSNNSNPVEDKDAVAFTCEPEVQNTTYLWWVNGQSLPVS

PRLQLSNGNMTLTLLSVKRNDAGSYECEIQNPASANRSDPVTLNVLY

GPDGPTISPSKANYRPGENLNLSCHAASNPPAQYSWFINGTFQQSTQ

ELFIPNITVNNSGSYMCQAHNSATGLNRTTVTMITVSGSAPVLSAVA

TVGITIGVLARVALI

An "anti-CEACAM antibody" is an antibody that can bind to at least CEACAM1, CEACAM5 and CEACAM6 proteins, and optionally any other CEACAM family protein.

"CD3" refers to an antigen which is expressed on T cells as part of the multimolecular T cell receptor (TCR) complex and which consists of a homodimer or heterodimer formed from the association of two or four receptor chains: CD3 epsilon, CD3 delta, CD3 zeta and CD3 gamma. Human CD3 epsilon comprises the amino acid sequence of SEQ ID NO: 5. All references to proteins, polypeptides and protein fragments herein are intended to refer to the human version of the respective protein, polypeptide or protein fragment unless explicitly specified as being from a non-human species. Thus, "CD3" means human CD3 unless specified as being from a non-human species, e.g., "mouse CD3" "monkey CD3," etc.

(Human CD3 epsilon):
SEQ ID NO: 5
MQSGTHWRVLGLCLLSVGVWGQDGNEEMGGITQTPYKVSISGTTVI

LTCPQYPGSEILWQHNDKNIGGDEDDKNIGSDEDHLSLKEFSELEQ

SGYYVCYPRGSKPEDANFYLYLRARVCENCMEMDVMSVATIVIVDI

CITGGLLLLVYYWSKNRKAKAKPVTRGAGAGGRQRGQNKERPPPVP

NPDYEPIRKGQRDLYSGLNQRRI

"Bispecific anti-CEACAM1/anti-CD3 antibody", CEACAM1/CD3 antibody, CEACAM1×CD3 antibody and the like refer to an antibody that binds CEACAM1 and CD3.

"Bispecific anti-CEACAM/anti-CD3 antibody", CEACAM/CD3 antibody, CEACAM×CD3 antibody and the like refer to an antibody that can bind CD3 and at least CEACAM1, CEACAM5 and CEACAM6 proteins, and optionally any other CEACAM family protein.

"In combination with" means that two or more therapeutics are administered to a subject together in a mixture, concurrently as single agents or sequentially as single agents in any order.

"CEACAM positive cancer" refers to a cancer tissue or a cancer cell that displays measurable level of CEACAM1 and/or CEACAM5 and/or CEACAM6 and/or any other CEACAM family protein. Level of a protein may be measured using well known assays using, for example ELISA, immunofluorescence, flow cytometry or radioimmunoassay on live or lysed cells. In one embodiment, the CEACAM positive cancer refers to a cancer tissue or a cancer cell that displays measurable level of CEACAM1. In another embodiment, the CEACAM positive cancer refers to a cancer tissue or a cancer cell that displays measurable level of CEACAM5. In another embodiment, the CEACAM positive cancer refers to a cancer tissue or a cancer cell that displays measurable level of CEACAM6.

A "cancer cell" or a "tumor cell" refers to a cancerous, pre-cancerous or transformed cell, either in vivo, ex vivo, or in tissue culture, that has spontaneous or induced phenotypic changes. These changes do not necessarily involve the uptake of new genetic material. Although transformation may arise from infection with a transforming virus and incorporation of new genomic nucleic acid or uptake of exogenous nucleic acid, it can also arise spontaneously or following exposure to a carcinogen, thereby mutating an endogenous gene. Transformation/cancer is exemplified by morphological changes, immortalization of cells, aberrant growth control, foci formation, proliferation, malignancy, modulation of tumor specific marker levels, invasiveness, tumor growth in suitable animal hosts such as nude mice, and the like, in vitro, in vivo, and ex vivo (Freshney, Culture of Animal Cells: A Manual of Basic Technique (3rd ed. 1994)).

"Treat" or "treatment" refers to both therapeutic treatment and prophylactic or preventative measures, wherein the object is to prevent or slow down (lessen) an undesired physiological change or disorder. Beneficial or desired clinical results include alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if a subject was not receiving treatment. Those in need of treatment include those already with the condition or disorder as well as those prone to have the condition or disorder or those in which the condition or disorder is to be prevented.

Generation of Antibodies

Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for CEACAM1 and the other is for any other antigen. In certain embodiments, one of the binding specificities is for CEACAM5 and the other is for any other antigen. In certain embodiments, one of the binding specificities is for CEACAM6 and the other is for any other antigen. In certain embodiments, bispecific antibodies may bind to two different epitopes of CEACAM1 or CEACAM5 or CEACAM6. Bispecific antibodies may also be used to localize cytotoxic agents to cells which express CEACAM1 or CEACAM5 or CEACAM6. Bispecific antibodies can be prepared as full-length antibodies or antibody fragments.

Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity) but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif ; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S, and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

Recombinant Methods and Compositions

Antibodies may be produced using recombinant methods and compositions, e.g., as described in U.S. Pat. No. 4,816,567. In one embodiment, isolated nucleic acid encoding an anti-CD122 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CD122 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CD122 antibody nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR$^-$ CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Modification of Antibodies

The antibodies of the invention may be subjected to one or more modifications known in the art, which may be useful for manipulating storage stability, pharmacokinetics, and/or any aspect of the bioactivity of the peptide, such as, e.g., potency, selectivity, and drug interaction. Chemical modification to which the peptides may be subjected includes, without limitation, the conjugation to a peptide of one or more of polyethylene glycol (PEG), monomethoxy-polyethylene glycol, dextran, poly-(N-vinyl pyrrolidone) polyethylene glycol, propylene glycol homopolymers, a polypropylene oxide/ethylene oxide co-polymer, polypropylene glycol, polyoxyethylated polyols (e.g., glycerol) and polyvinyl alcohol, colominic acids or other carbohydrate based polymers, polymers of amino acids, and biotin derivatives. PEG conjugation of proteins at Cys residues is disclosed, e.g., in Goodson, R. J. & Katre, N. V. (1990) Bio/Technology 8, 343 and Kogan, T. P. (1992) Synthetic Comm. 22, 2417.

Other useful modifications include, without limitation, acylation, using methods and compositions such as described in, e.g., U.S. Pat. No. 6,251, 856, and WO 00/55119.

Therapeutic Administration

The antibodies of the present invention may be administered individually or in combination with other pharmacologically active agents. It will be understood that such combination therapy encompasses different therapeutic regimens, including, without limitation, administration of multiple agents together in a single dosage form or in distinct, individual dosage forms. If the agents are present in different dosage forms, administration may be simultaneous or near-simultaneous or may follow any predetermined regimen that encompasses administration of the different agents.

For example, when used to treat cancer, the antibodies of the invention may be advantageously administered in a combination treatment regimen with one or more agents, including, immunotherapeutic agents.

Methods of Administration

The antibodies of this invention may be administered as pharmaceutical compositions comprising standard carriers known in the art for delivering proteins and peptides and by gene therapy. Preferably, a pharmaceutical composition includes, in admixture, a pharmaceutically (i. e., physiologically) acceptable carrier, excipient, or diluent, and one or more of molecules targeting CEACAM1, or CEACAM5, or CEACAM6, as an active ingredient. In one embodiment, the CEACAM1 targeting molecule is an antibody that specifically binds to CEACAM1. In one embodiment, the CEACAM5 targeting molecule is an antibody that specifically binds to CEACAM5. In one embodiment, the CEACAM6 targeting molecule is an antibody that specifically binds to CEACAM6. The preparation of pharmaceutical compositions that contain peptides as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients that are pharmaceutically (i.e., physiologically) acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH-buffering agents, which enhance the effectiveness of the active ingredient.

A CEACAM targeting molecule can be formulated into a pharmaceutical composition as neutralized physiologically acceptable salt forms. In one embodiment, the CEACAM targeting molecule is an antibody that specifically binds to CEACAM. Suitable salts include the acid addition salts (i.e., formed with the free amino groups of the peptide molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The pharmaceutical compositions can be administered systemically by oral or parenteral routes. Non-limiting parenteral routes of administration include subcutaneous, intramuscular, intraperitoneal, intravenous, transdermal, inhalation, intranasal, intra-arterial, intrathecal, enteral, sublingual, or rectal. Due to the labile nature of the amino acid sequences parenteral administration is preferred. Preferred modes of administration include aerosols for nasal or bronchial absorption; suspensions for intravenous, intramuscular, intrasternal or subcutaneous, injection; and compounds for oral administration.

Intravenous administration, for example, can be performed by injection of a unit dose. The term "unit dose" when used in reference to a pharmaceutical composition of the present invention refers to physically discrete units suitable as unitary dosage for humans, each unit containing a predetermined quantity of active material calculated to produce the desired therapeutic effect in association with the required diluent; i.e., liquid used to dilute a concentrated or pure substance (either liquid or solid), making that substance the correct (diluted) concentration for use. For injectable administration, the composition is in sterile solution or suspension or may be emulsified in pharmaceutically-and physiologically-acceptable aqueous or oleaginous vehicles, which may contain preservatives, stabilizers, and material for rendering the solution or suspension isotonic with body fluids (i.e., blood) of the recipient.

Excipients suitable for use are water, phosphate buffered saline, pH 7.4, 0.15 M aqueous sodium chloride solution, dextrose, glycerol, dilute ethanol, and the like, and mixtures thereof. Illustrative stabilizers are polyethylene glycol, proteins, saccharides, amino acids, inorganic acids, and organic acids, which may be used either on their own or as admixtures. The amounts or quantities, as well as routes of administration, used are determined on an individual basis, and correspond to the amounts used in similar types of applications or indications known to those of skill in the art.

Pharmaceutical compositions are administered in a manner compatible with the dosage formulation, and in a therapeutically effective amount. The quantity to be administered depends on the subject to be treated and capacity of the subject's immune system to utilize the active ingredient. Precise amounts of active ingredient required to be administered depend on the judgment of the practitioner and are specific for each individual.

Further guidance in preparing pharmaceutical formulations can be found in, e.g., Gilman et al. (eds), 1990, Goodman and Gilman's: The Pharmacological Basis of Therapeutics, 8th ed., Pergamon Press; and Remington's Pharmaceutical Sciences, 17th ed., 1990, Mack Publishing Co., Easton, Pa.; Avis et al. (eds), 1993, Pharmaceutical Dosage Forms: Parenteral Medications, Dekker, New York; Lieberman et al. (eds), 1990, Pharmaceutical Dosage Forms: Disperse Systems, Dekker, N.Y.

The present invention further contemplates compositions comprising an IR agonist or antagonist peptide, and a physiologically acceptable carrier, excipient, or diluent as described in detail herein.

The following examples illustrate the invention. These examples should not be construed as to limit the scope of this invention. The examples are included for purposes of illustration and the present invention is limited only by the claims.

EXAMPLE 1

Generation of Anti-CEACAM mAbs 1.1 Generation of Anti-CEACAM mAbs using OmniRats®

The OmniRat® contains a chimeric human/rat IgH locus (comprising 22 human VHS, all human D and $J_H$ segments in natural configuration linked to the rat $C_H$ locus) together with fully human IgL loci (12 Vκs linked to Jκ-Cκ and 16 Vλs linked to Jλ-Cλ). (see e.g., Osborn, et al. (2013) J Immunol 190(4): 1481-1490). Accordingly, the rats exhibit reduced expression of rat immunoglobulin, and in response to immunization, the introduced human heavy and light chain transgenes undergo class switching and somatic mutation to generate high affinity chimeric human/rat IgG monoclonal antibodies with fully human variable regions. The preparation and use of OmniRat®, and the genomic modifications carried by such rats, is described in WO14/093908.

OmniRats were immunized with the extracellular domain of human CEACAM1, fused to a 10-His tag (R&D Systems, #2244-CM, SEQ ID NO: 6), and boosted with the same antigen every three to four days with bilateral injections at the base of the tail, hock, axillary, and ear. Following a 48 day immunization regimen, lymph nodes from the rats were harvested and used to generate hybridomas and the hybridoma supernatants were screened as described below.

SEQ ID NO: 6 qlttesmpfnvaegkevlllvhnlpqqlfgyswykgervdgnrqiv gyaigtqqatpgpansgretiypnaslliqnvtqndtgfytlqvik sdlvneeatgqfhvypelpkpsissnnsnpvedkdavaftcepetq dttylwwinnqslpvsprlqlsngnrdtllsvtmdtgpyeceiqnp vsanrsdpvtlnytygpdtptispsdtyyrpganlslscyaasnpp aqyswlingtfqqstqelfipnitvnnsgsytchannsvtgcnrtt vktiivtelspvvakpqikaskttvtgdkdsvnitcstndtgisir wffknqslpssermklsqgnttlsinpvkredagtywcevfnpisk nqsdpimlnvnynalpqenglspghhhhhhhhhh 1.2 Generation of Anti-CEACAM mAbs using Phage Display Libraries CEACAM1 binding Fabs were selected using standard methods from two sets of de novo pIX phage display libraries as described in Shi et al., J Mol Biol 397:385-96, 2010 and WO2009/085462). Briefly, two sets of libraries, referred to as V3.0 and V5.0, were generated by diversifying human scaffolds where germline VH genes IGHV1-69*01, IGHV3-23*01 and IGHV5-51*01 were recombined with the human IGHJ-4 minigene via the H3 loop (IGHJ-6 minigene was also used in V5.0), and human germline VLkappa genes 012 (IGKV1-39*01), L6 (IGKV3-11*01), A27 (IGKV3-20*01), and B3 (IGKV4-1*01) were recombined with the IGKJ-1 minigene to assemble complete VH and VL domains. Positions in the heavy and light chain variable regions around the H1, H2, L1, L2 and L3 loops in frequent contact with protein and peptide antigens were chosen for diversification. Sequence diversity at selected positions was limited to residues occurring at each position in the IGHV or IGLV germline gene families of the respective IGHV or IGLV genes. Diversity at the H3 loop was generated by utilizing short to mid-sized synthetic loops of lengths 7-14 amino acids for V3.0 libraries, and lengths 6-19 amino acids for V5.0 libraries. The amino acid distribution at H3 was designed to mimic the observed variation of amino acids in human antibodies. The scaffolds utilized to generate libraries were named according to their human VH and VL germline gene origin. For both V3.0 and V5.0 sets, each of the three heavy chain libraries were combined with the four germline light chains or germline light chain libraries to generate 12 unique VH:VL combinations for each set of libraries which are used for selection experiments.

V Region Cloning. Total RNA from hybridoma cell lysates of phage were purified using RNeasy 96 kit (Qiagen) following the manufacturer's protocol. The resulting RNA was quantitated using Drop Sense and either stored at −80° C. or used for cDNA synthesis using Invitrogen SuperScript III First-Strand Synthesis System by RT-PCR (Invitrogen). The first strand cDNA synthesis was carried out using gene specific primers annealed to the constant regions of heavy, kappa, and lambda chains, respectively. The RT-PCR reaction mixture comprised of up to 3 μg of purified RNA, gene specific primer, dNTP mix, reaction buffer, 25 mM $MgCl_2$, DTT, RNaseOUT™ (40 U/μl, Invitrogen), and SuperScript™ III RT (200 U/μl, Invitrogen Cat #18080-051) was incubated at 50° C. for 50 minutes and 85° C. for 5 minutes. The resulting single-stranded cDNA was stored at −20° C., or used directly for PCR amplification. The PCR reaction was carried out using Platinum Pfx polymerase (Invitrogen). The v-region fragments were amplified by forward and reverse primers annealing to the leader sequences and constant regions of heavy, kappa and lambda chains, respectively, using optimized PCR conditions. The resulting PCR fragments were sequenced, the amino acid sequences of the recovered v-regions were codon optimized and cloned into the pUnder-based expression vector carrying the IgG2 Sigma constant region with F405L kappa mutations.

Expi293 Small Scale Transfection and Purification. Select antibodies identified from the immunization campaigns or phage display were cloned and expressed as IgG2 Sigma and purified via small 2 ml scale. Expi293™ cells (ThermoFisher Scientific) were seeded at $1.25×10^5$-$2.25×10^5$ viable cells/mL density in Expi293™ Expression Medium and cultured in 125 mL-2 L shake flasks at 37° C., 7% $CO_2$. Cells were sub-cultured when density reached the log phase growth at $3×10^6$-$5×10^6$ viable cells/mL with a 98-99% viability.

On day of transfection, the viable cell density and percent viability was determined. Cells were transfected at a density of $3×10^6$ viable cells/mL following manufacturer's Transfection protocol (ThermoFisher Publication Number MAN0007814). Culture were harvested on Day 6 post-transfection by centrifugation at 850×G for 15 minutes before purification. Antibodies were purified from the clarified supernatants using mAb Select Sure resin (GE Healthcare) and dialyzed into PBS. Protein concentrations were determined by A280 measurement on the filtrate using a DropSense Instrument (Trinean).

EXAMPLE 2

Characterization of Binding of Anti-CEACAM mAbs to CEACAM1

2.1 Binding to recombinant CEACAM1. Hybridoma supernatants and phage display derived antibodies were screened by ELISA for binding to the recombinant CEACAM1 protein (R&D Systems, Minneapolis, Minn.).

Plates were coated with 50 μl of 1 μg/ml of CEACAM1 (#2244-CM, R&D Systems) overnight at 4° C. The next day, in 16 h, plates were blocked with 200 μl 0.4% bovine serum albumin (BSA) (Sigma, A9647) in PBS for 1 hr at room temperature. Plates were washed once with 300 μl of 0.02% Tween-20 in PBS on a Biotek plate washer. 1/2 log dilutions of CEACAM mAbs starting from 10 μg/ml to 0.0001 ug/ml in 0.4% BSA, or PBS only, were plated for each antibody. 50 μl of each dilution were added to coated plates. Plates were incubated at room temp for approx 30 min. Plates were then washed 3 times with 300 μl of 0.02% Tween-20 in PBS using a Biotek plate washer. 50 ul of 1:10,000 Goat anti huFc'2-HRP (Jackson ImmunoResearch, cat #109-036-098) was added to plates. Plates were incubated at room temp for approximately 30 min. Plates were then washed 3 times with 300 ul of PBS/0.02% Tween-20 on a Biotek plate washer. 50 μl of 3,3',5,5'-Tetramethylbenzidine (TMB, Sigma T0440) were added, allowed for color development, followed by adding 50 ul of 4N $H_2SO_4$. Plates were analyzed at 450 nm using EnVision Microplate Reader (PerkinElmer). Isotype control (CNT08939 antibody, specific to RSV virus, having the human IgG2 sigma backbone) was plated on last 3 plates at a concentration 10 μg/ml. Absorbance at 450 nm (FIG. 2) was analyzed using XY scatter plots and non-linear fit curves were generated after log transformation, and EC50 values were calculated, using GraphPad Prism (GraphPad Software, San Diego, Calif.). For several antibodies the EC50 could not be calculated using GraphPad Prism due to poor curve fit; in these cases the EC50 values were visually estimated at the midpoint of the available curve. EC50 values for binding to recombinant CEACAM1 are represented in Table 1.

TABLE 1

EC50 values for anti-CEACAM1 mAbs binding to recombinant CEACAM1, as determined by ELISA.

| mAb ID | CEACAM1 EC50, g/mL |
|---|---|
| CCMB02.004 | 17.06 |
| CCMB03.004 | 19.91 |
| CCMB04.004 | 11.19 |
| CCMB07.004 | 12.19 |
| CCMB09.004 | 7.296 |
| CCMB18.004 | 6.907 |
| CCMB20.004 | 18.62 |
| CCMB23.004 | 45.47 |
| CCMB35.004 | 55.64 |
| CCMB42.004 | 6.201 |
| CCMB61.004 | 26.62 |
| CCMB66.004 | 6.706 |

2.2 Binding of anti-CEACAM mAbs to Cells Overexpressing CEACAM1.

Binding of anti-CEACAM mAbs to HEK293K cells overexpressing CEACAM1 was evaluated.

Generation of HEK293T Cells Overexpressing CEACAM1.

HEK293T (ATCC, Manassas, Va.) cells overexpressing full length CEACAM1 were generated using lentiviral vectors encoding CEACAM1 (SEQ ID NO: 1) and a GFP tag (LPP-U0045-Lv105-200, Genecopeoia). Cells were washed with fresh medium and then suspended in Opti-MEM (Thermo) containing 8 ug/ml polybrene at $2 \times 10^6$ cells/ml. In a 12-well tissue culture plate, 0.5 ml of the cell suspension ($1 \times 10^6$ cells) was added per well. Viral particles were added at 0.3, 1.0, 3.0 and 5.0 units of multiplicity of infection (MOI). Plates were gently mixed and incubated for 20 min in the hood at room temp. Plates were centrifuged for 90 minutes at 1500 g at 37° C. 0.5 ml fresh Opti-MEM media were added to the cells. Plates were incubated at 37° C. for 48-72 hours. Cells were checked for the presence of GFP signal under UV light. At 80-90% confluency, cells were transferred to a bigger 100 mm dish or T-75 and the media was replaced with selection media containing 0.5 ug/mL puromycin. Cells were monitored and kept on selection media (Opti-MEM supplemented with 0.5 µg/mL puromycin) for the next few days or weeks until most cells were viable under selection media. Cells were stained for the expression protein using labeled antibodies and prepared for FACS analysis. When sufficient expression levels were reached, stable cells were frozen down or sort for high/medium or low expressing cells. Selection was done for 1 week using 0.5 µg/ml of Puromycin.

Flow Cytometry

Flow cytometry was used to confirm surface expression of CEACAM-1. For flow cytometry staining cells were blocked in FACS stain buffer containing human Fc block (Miltenyi Biotech, 1:20) and LIVE/DEADTM Fixable Near-IR Dead Cell Stain Kit (Invitrogen, 1:500) for 15 mins at room temperature. Cells were then stained with one of the following anti-human antibodies for 30 mins at 4° C. in 50 ul of FACS stain buffer/well: phycoerythrin (PE)-conjugated anti-CEACAM-1 antibody (R&D Systems, cat#FAB2244P), 1:50), phycoerythrin-conjugated Mouse IgG2b Isotype Control (Biolegend), and Unlabeled Anti-CEACAM-1 (specific to CD66a) (Millipore, cat #MABT65, 1:50). Antibody and Mouse IgG1 Isotype were detected with a PE anti-mouse secondary antibody (Jackson ImmunoResearch, 1:200).

CEACAM1 overexpressing cells were then subcloned and sorted for purified populations of CEACAM1 positive cells, using standard techniques (FIG. 3). These cells were then used to generate binding curves by flow cytometry (FIG. 4). CEACAM antibodies binding to the surface of overexpressing cells were detected using a goat anti-human Fc antibody (Jackson ImmunoResearch, cat #109-606-098). Most antibodies bound very well to the CEACAM-1 expressing HEK293T cells and did not titer out, meaning the concentration where binding was undetectable was not reached (Table 2).

TABLE 2

EC50 calculations for anti-CEACAM-1 antibodies binding to CEACAM-1 expressing HEK293T cells.

| mAb ID | CEACAM1 EC50, (ng/mL) |
|---|---|
| CCMB02.004 | Potent binder, did not titer out |
| CCMB03.004 | Potent binder, did not titer out |
| CCMB04.004 | Potent binder, did not titer out |
| CCMB07.004 | Potent binder, did not titer out |
| CCMB09.004 | Potent binder, did not titer out |
| CCMB18.004 | Potent binder, did not titer out |
| CCMB20.004 | Potent binder, did not titer out |
| CCMB23.004 | 4.194 |
| CCMB35.004 | 27.5 |
| CCMB42.004 | Potent binder, did not titer out |
| CCMB61.004 | 35.34 |
| CCMB66.004 | Potent binder, did not titer out |

EXAMPLE 3

Characterization of Binding of Anti-CEACAM mAbs to CEACAM5 and CEACAM6

3.1 Binding to recombinant CEACAM5 and CEACAM6. Cross-screening for specificity of purified phage and hybridoma antibodies to recombinant CEACAM5 (R&D Systems #4128-CM) and CEACAM6 (R&D Systems #3934-CM) was performed using ELISA, according to the protocol described in Example 2. Binding curves for binding of mAbs to CEACAM5 are shown on FIG. 5a, and to CEACAM6 on FIG. 5b. CEACAM1 antibodies had variable binding to CEACAM5 and CEACAM6 proteins, demonstrating some cross-reativity (Table 3).

TABLE 3

EC50 values for anti-CEACAM1 mAbs binding to recombinant CEACAM5 or CEACAM6, as determined by ELISA.

| mAb ID | CEACAM5 EC50, (ug/mL) | CEACAM6 EC50, (ug/mL) |
|---|---|---|
| CCMB02.004 | 50 | >10000 |
| CCMB03.004 | 16.44 | 5 |
| CCMB04.004 | 6.463 | 5.571 |
| CCMB07.004 | 9.773 | >10000 |
| CCMB09.004 | 4.461 | 5.131 |
| CCMB18.004 | 4.32 | 6.054 |
| CCMB20.004 | 4.268 | >10000 |
| CCMB23.004 | >10000 | >10000 |
| CCMB35.004 | >10000 | >10000 |
| CCMB42.004 | 1.141 | >10000 |
| CCMB61.004 | >10000 | 1243 |
| CCMB66.004 | 1688 | >10000 |

3.2 Binding to cells overexpressing CEACAM5 and CEACAM6. HEK293T cells overexpressing CEACAM5 and CEACAM6 were generated using transduction with lentiviral vectors encoding CEACAM5 (LPP-G0056-Lv105-100, Genecopeoia) and CEACAM6 (LPP-G0304-Lv105-100, Genecopeoia), according to the protocol described in Example 2. Flow cytometry was used to confirm expression of CEACAM5 or CEACAM6 on the surface of the cells (FIGS. 6a and 6b), according to the procedure described in Example 2. CEACAM-5 stable pools were sorted using the FACS Aria to eliminate low protein expressers. PE-conjugated Anti-CEACAM-1,5,6 (Biolegend cat #342358, 1:50) and PE-conjugated Mouse IgG2b Isotype Control (Biolegend) were used for CEACAM5 and CEACAM6 cell lines. Binding curves for binding of mAbs to cells overexpressing CEACAM5 are shown on FIG. 7a, and to cells overexpressing CEACAM6 on FIG. 7b. The results suggested that some CEACAM1 antibodies had significant cross-reativity and bound to cells expressing CEACAM5 or CEACAM6, but other CEACAM1 antibodies had little or no binding to these cells (Table 4).

TABLE 4

EC50 values for anti-CEACAM1 mAbs binding to CEACAM5 or CEACAM6 expressing HEK293T cells, as determined by flow cytometry.

| mAb ID | CEACAM5 EC50, (ng/mL) | CEACAM6 EC50, (ng/mL) |
|---|---|---|
| CCMB02.004 | Potent binder, did not titer out | No binding |
| CCMB03.004 | Potent binder, did not titer out | 5.153 |
| CCMB04.004 | Potent binder, did not titer out | 10.91 |
| CCMB07.004 | Potent binder, did not titer out | No binding |
| CCMB09.004 | Potent binder, did not titer out | 15.78 |
| CCMB18.004 | Potent binder, did not titer out | 11.82 |
| CCMB20.004 | Potent binder, did not titer out | No binding |
| CCMB23.004 | No binding | No binding |
| CCMB35.004 | No binding | No binding |
| CCMB42.004 | Potent binder, did not titer out | No binding |
| CCMB61.004 | No binding | No binding |
| CCMB66.004 | No binding | No binding |

EXAMPLE 4

Structural Characterization of Anti-CEACAM mAbs

The cDNA sequences and amino acid translations of the antibodies were obtained using standard techniques. After polypeptide sequence determination, some antibody cDNAs encoding the variable regions or full-length antibodies were codon optimized using standard methods for scale-up expression.

Table 5 shows the heavy chain CDR amino acid sequences of select anti-CEACAM antibodies.

Table 6 shows the light chain CDR amino acid sequences of select anti-CEACAM antibodies.

Table 7 shows the VH and VL amino acid sequences of select anti-CEACAM antibodies.

TABLE 5

| mAb | HCDR1 sequence (SEQ ID NO:) | HCDR2 sequence (SEQ ID NO:) | HCDR3 sequence (SEQ ID NO:) |
|---|---|---|---|
| mAb 1 | NYAMN (7) | VISGSGSGTYYADSVKG (8) | PPPMVRGVIITIGNY (9) |
| mAb 2 | SYGLS (13) | WINTNTGNPTYAQGFTG (14) | KGIWGPFDY (15) |
| mAb 3 | NYGVN (19) | WINTNTGNPTYVQGFTG (20) | KGIWGPFDH (21) |
| mAb 4 | NYAMN (25) | VISGSGSGTYYADSVKG (26) | PPPMVRGVIITIGNY (27) |
| mAb 5 | SGGHYWS (31) | NIYYSGSTHYNPSLKS (32) | GRLLWFGEPQDFQH (33) |
| mAb 6 | DYGMN (37) | WINTNTGNPTYAQGFTG (38) | KAIWGWFDP (39) |
| mAb 7 | NYAMT (43) | SISGTSANTYYADAVKG (44) | PILTLFGELPLDY (45) |
| mAb 8 | RTSYYWG (49) | TIYYSGSTYYNPSLKS (50) | QIAVGAHRFDY (51) |
| mAb 9 | DYAMN (55) | SISGTGGSTYYADSLKG (56) | DIAVGVTAYFDH (57) |
| mAb 10 | TYGMS (61) | TISGSGDNTYYADSVKG (62) | GGLLWFGELPYPFDY (63) |
| mAb 11 | SYAMN (67) | AISGSGGSTYYADSVKG (68) | DFAVGATTSFDY (69) |
| mAb 12 | SYWIG (73) | IIYPGDSDTRYSPSFQG (74) | GYPAPTVNDLDY (75) |

TABLE 6

| mAb | LCDR1 sequence (SEQ ID NO:) | LCDR2 sequence (SEQ ID NO:) | LCDR3 sequence (SEQ ID NO:) |
|---|---|---|---|
| mAb 1 | RASQSVSVNLA (10) | GASTRAT (11) | QQYNNWPFT (12) |
| mAb 2 | KSSQNVLYSSNNKNYLA (16) | WASTRES (17) | QQYFSSPWT (18) |
| mAb 3 | KSSQSVLYSSNNRLYLA (22) | WASTRES (23) | QQYYSNPWT (24) |
| mAb 4 | RASQSVSVNLA (28) | GASTRAT (29) | QQYNNWPFT (30) |
| mAb 5 | KSSQSVLYSSNNKNYLT (34) | WASTRES (35) | QQYYSTPT (36) |
| mAb 6 | KPSQSVLYRSNNKNYLA (40) | WASTRES (41) | QQYYSTPCS (42) |
| mAb 7 | RASQSVSSNLA (46) | GASTRAT (47) | QQYNNWPLT (48) |
| mAb 8 | RASQGISSYLA (52) | AASTLQS (53) | QQLNSYPWT (54) |
| mAb 9 | QGDSLRTYSAS (58) | GKNNRPS (59) | NSRDSRGNLLVV (60) |
| mAb 10 | TGTSSDVGGYNYVS (64) | DVSNRPS (65) | SSYISTSTLYV (66) |
| mAb 11 | QGDSLRSYYVS (70) | GKNNRPS (71) | NSRDSSNHLVV (72) |
| mAb 12 | RASQSISSYLN (76) | AASSLQS (77) | QQSYSTPLT (78) |

TABLE 7

| mAb | VH sequence (SEQ ID NO:) | VL sequence (SEQ ID NO:) |
|---|---|---|
| CCMB02.004 | EVQLLESGGGLVQPGGSLRLSCA ASGFTFINYAMNWVRLTPGKGL EWVSVISGSGSGTYYADSVKGRF TVSRDNSKNTLYLQMNSLRVED TAIYYCASPPPMVRGVIITIGNYW GQGALVTVSS (79) | EIVMTQSPATLSVSPGERATLSC RASQSVSVNLAWYQQKPGQAP RLLIYGASTRATGIPARFSGSGSG TEFTLTISSLQSEDFAVYYCQQY NNWPFTFGPGTKVDIK (80) |
| CCMB03.004 | QVQLVQSGSELRTPGASVKVSCK ASGYTFTSYGLSWVRQAPGQGL EWMGWINTNTGNPTYAQGFTGR FVFSLDTSVSTAYLQISSLKAEDT AVYYCARKGIWGPFDYWGQGTL VTVSS (81) | DIVMTQSPDSLAVSLGERATINC KSSQNVLYSSNNKNYLAWYQQ KPGQPPKLLIYWASTRESGVPDR FSGSGSGTDFTLTISCLQAEDVA VYYCQQYFSSPWTFGQGKVEI K (82) |
| CCMB04.004 | QVQLVQSGSELKKPGASVKVSC KASGYTFTNYGVNWVRQAPGQ GLEWMGWINTNTGNPTYVQGFT GRFVFSLDTSVTTAYLHISSLKAE DTAVYFCARKGIWGPFDHWGQG TLVTVSS (83) | DIVMTQSPDSLAVSLGERATINC KSSQSVLYSSNNRLYLAWYQQR PGQPPKLLIYWASTRESGVPDRF SGSGSGTDFTLTISSLQAEDVAV YYCQQYYSNPWTFGGGTKVEIK (84) |
| CCMB07.004 | EVQLLESGGGLVQPGGSLRLSCA ASGFTFTNYAMNWVRLAPGKGL EWVSVISGSGSGTYYADSVKGRF TVSRDNSKNTLYLQMNSLRVED TAIYYCASPPPMVRGVIITIGNYW GQGALVTVSS (85) | EIVMTQSPATLSVSPGERATLSC RASQSVSVNLAWYQQKPGQAP RLLIYGASTRATSIPTRFSGSGSG TEFTLTISSLQSEDFAVYYCQQY NNWPFTFGPGTKVEIK (86) |
| CCMB09.004 | QVQLQESGPGLVKPSQTLSLTCT VTGDSIRSGGHYWSWIRQHPGK GLEWIGNIYYSGSTHYNPSLKSR LTISVDTSKNQFSLKVSSVTAADT AVYYCARGRLLWFGEPQDFQH WGQGTLVTVSS (87) | DIVMTQSPDSLAVSLGERATINC KSSQSVLYSSNNKNYLTWYQQK PGQPPKLLIYWASTRESGVPDRF SGSGSGTDFTLTISSLQAEDVAV YYCQQYYSTPTFGQGTKLEIK (88) |
| CCMB18.004 | QVQLVQSGSELKKPGASVKVSC KASGYTLTDYGMNWVRQAPGQ GLQWMGWINTNTGNPTYAQGFT GRFVFSLDTSVSTAYLQISSLKTE DTAVYYCARKAIWGWFDPWGQ GTLVTVSS (89) | DIVMTQSPDSLAVSLGERATINC KPSQSVLYRSNNKNYLAWYQQ KPGQPPKLLIHWASTRESGVPDR FSGSGSGTDFTLTISSLQAEDVA VYYCQQYYSTPCSFGQGTKLEI K (90) |
| CCMB20.004 | EVQLLESGGGLVQPGESLRLSCA ASGFTFNNYAMTWVRQAPGKGL DWVSSISGTSANTYYADAVKGR FTISRDNSMTTLYLQMNSLRAED TAVYYCAKPILTLFGELPLDYWG QGTLVTVSS (91) | EIVMTQSPATLSVSPGERATLSC RASQSVSSNLAWYQQKTGQAPR LLIYGASTRATAFPARFSGSGSG TEFTLTISSLQSEDFAVYYCQQY NNWPLTFGGGTKVEIK (92) |
| CCMB23.004 | QLQLQESGPGLVKPSETLSLTCT VSADSISRTSYYWGWIRQPPGKG LEWIGTIYYSGSTYYNPSLKSRVT ISVDTSRNHFSLTLNSVTAADTA VYYCARQIAVGAHRFDYWGQGT LVTVSS (93) | DIQLTQSPSFLSASVGDRVTITCR ASQGISSYLAWYQQKPGKAPKL LIYAASTLQSGVPSRFSGSGSGT EFTLTISSLQPEDFATYYCQQLN SYPWTFGQGTKVEIK (94) |
| CCMB35.004 | EVQLLESGGGLVQPGESLRLSCA ASGLTFSDYAMNWVRQAPGKGL YWVSSISGTGGSTYYADSLKGRF TISRDNSKNTLYLQMNSLRAEDT AVYYCAKDIAVGVTAYFDHWG QGTLVTVSS (95) | SSELTQDPAVSVALGQTVRITCQ GDSLRTYSASWYQQKPGQAPVL VIYGKNNRPSGIPDRFSGSSSGN TASLTITGAQAEDEADYYCNSR DSRGNLLVVFGGGTKLTVL (96) |

TABLE 7-continued

| mAb | VH sequence (SEQ ID NO:) | VL sequence (SEQ ID NO:) |
|---|---|---|
| CCMB42.004 | EVQLLESGGGLVQPGGSLRLSCA ASGFTFNTYGMSWARQAPGKGL EWVSTISGSGDNTYYADSVKGRF TISRDNSKNTLYLQINSLRAEDTA VYYCAKGGLLWFGELPYPFDYW GQGTLVTVSS (97) | QSALTQPASVSGSPGQSITISCTG TSSDVGGYNYVSWYQQHPGKA PKLMIYDVSNRPSGVSNRFSGSK SDNTASLTISGLQAEDEADYYCS SYISTSTLYVFGIGTKVTVL (98) |
| CCMB61.004 | EVQLLESGGGLVQPGGSLRLSCA ASGFTFSSYAMNWVRQAPGKGL EWVSAISGSGGSTYYADSVKGRF TISRDNSKNTLYLQMNSLRAEDT AVYYCAKDFAVGATTSFDYWG QGSLVTVSS (99) | SSELTQDPAVSVALGQTVRITCQ GDSLRSYYVSWYQQKPGQAPTL VIYGKNNRPSGIPDRFSGSSSGN TPSLTITGAQAEDEADYYCNSRD SSNHLVVFGGRTKLTVL (100) |
| CCMB66.004 | EVQLVQSGAEVKKPGESLKISCK GSGYSFTSYWIGWVRQMPGKGL EWMGHYPGDSDTRYSPSFQGQV TISADKSISTAYLQWSSLKASDTA MYYCARGYPAPTVNDLDYWGQ GTLVTVSS (101) | DIQMTQSPSSLSASVGDRVTITC RASQSISSYLNWYQQKPGKAPK LLIYAASSLQSGVPSRFSGSGSGT DFTLTISSLQPEDFATYYCQQSY STPLTFGQGTKVEIK (102) |

EXAMPLE 5

Modulation of T Cell Activation and Effector Function by Anti-CEACAM mAbs

Anti-CEACAM antibodies were evaluated for their ability to modulate T cell activation and effector function. This was done by activating normal donor T cells with antibody specific for CD3 (OKT3, Janssen, engineered onto IgG1 backbone) in the presence or absence of CEACAM binding antibodies. Activity of T cells was evaluated by assessing differentiation, proliferation, and cytokine secretion. Representative samples that show variable modulation of T cell activation parameters are shown as examples below.

Peripheral blood mononuclear cell (PBMC) stimulation. PBMCs were thawed or isolated from fresh blood/leukopack (HemaCare, Northridge, Calif.) and washed with RPMI 1640 medium (Thermo), supplemented with GlutaMAX™ and 10% FBS (Thermo). Proliferation of PBMCs was evaluated using CellTrace™ Violet Cell Proliferation Kit (Thermo). PBMCs were counted and resuspended at $2 \times 10^6$/ml. 50 ul containing either anti-CEACAM antibody dilution in the medium or medium alone were added to the 96-well round bottom plate. 50 ul containing anti-CD3 or medium were added to the 96-well round bottom plate. Cells were plated at 100 ul or $2 \times 10^5$ cells per well. Plates were incubated for 3 days at 37° C.

Staining and cytometric analysis. After incubation, the plate was spun down, and 100 ul of supernatant was harvested for cytokine analysis. Cell pellets were resuspended in 50 ul BD FACS buffer (BD Biosciences) containing Fc block and Live/Dead stain (Life technologies #L34957). Plate was incubated for 15 min at room temperature and washed with 150 uL of BD FACS buffer. Cell pellets were resuspended in 50 ul of BD FACS buffer containing a cocktail of antibodies including anti-PD-1 antibodies, conjugated with Brilliant Violet (BV) 605™ (Biolegend #329923), anti-CD25 antibodies conjugated with BV650 (BD #563719), anti-CD4 antibodies conjugated with BV7119 (Biolegend #317440), anti-CD8 antibodies conjugated with BV785 (Biolegend #301045), and anti-CEACAM1 conjugated with allophycocyanin (APC, Biolegend #305312) for 30 min. Cells were washed with 150 uL of BD FACS buffer and permeabilized in 50 ul eBioscence FoxP3 buffer for 20 min. Cells were washed in 150 uL eBioscience FoxP3 perm/wash buffer then resuspended in eBioscience FoxP3 perm/wash buffer containing flow cytometry antibodies as per Flow Panel for 30 min. Cells were washed in 150 uL of eBioscience FoxP3 perm/wash buffer then fixed in 150 ul BD cytofix and analyzed on BD Fortessa flow cytometer. Cytokines were analyzed by running the Meso Scale Devices Human Th1/Th2 Tissue culture kit (MSD, K15010B). Briefly, supernatant from T cell cultures were incubated on the pre-coated and blocked 96-well plates for 1 hr, detection with the MSD Detection Antibody Blend for 1 hr, followed by washing and addition of Read Buffer. The plates were then read on the MSD Sector plate reader. Fluorescence values were used to calculate cytokine concentrations using a standard curve from the same plate.

The results demonstrated that CEACAM binding antibodies modulated all three types of T cell activation. First, the surface marker expression was induced on T cells in response to exposure to CEACAM1 antibodies in combination with anti-CD3 antibody (FIG. 8). Expression of PD-1 on the surface of T cell was used as a marker of activation of T cells (FIG. 8). Both CD4 and CD8 T cells had increased levels of PD-1 in the presence of CEACAM binding antibodies up to two-fold, as compared to CD3 alone ($p<0.0001$, ANOVA). Second, analysis of T cell proliferation demonstrated an increase in dividing cells by dilution of cell trace violet (CTV) ($p<0.0001$, ANOVA) (FIG. 9). Finally, ligation of CEACAM on T cells in the presence of CD3 stimulation increased the production of cytokines IFNγ (FIG. 10a, $p=0.0105$, ANOVA) and TNFα (FIG. 10b, $p=0.0146$, ANOVA).

EXAMPLE 6

Modulation of T Cell Responses to Tumors in Mouse Models by Anti-CEACAM1 Antibodies Anti-CEACAM antibodies can also be used to demonstrate efficacy in humanized mouse models. Blocking CEACAM interaction on T cell improves activation and function on T cells and may therefore play a role in growth inhibition or regression of tumors in humanized mouse models. Administration of anti-CECAM antibodies concurrently, before, or after T cell engraftment to mice bearing tumors from either hematological malignancies such as leukemias, lymphomas, or myeloma, or solid tumor such as melanoma, prostate cancer, or non-small cell lung cancer cell lines may increase the ability of those T cells to control tumor growth.

What is claimed is:

1. An isolated anti-CEACAM (Carcinoembryonic antigen-related cell adhesion molecule) antibody or an antigen-binding fragment thereof, selected from the group consisting of
 an isolated anti-CEACAM antibody or an antigen-binding fragment thereof, comprising a HCDR1, a HCDR2, a HCDR3, a LCDR1, a LCDR2 and a LCDR3 of SEQ ID NOs: 7, 8, 9, 10, 11, and 12, respectively;
 an isolated anti-CEACAM antibody or an antigen-binding fragment thereof, comprising a HCDR1, a HCDR2, a HCDR3, a LCDR1, a LCDR2 and a LCDR3 of SEQ ID NOs: 13, 14, 15, 16, 17, and 18, respectively;
 an isolated anti-CEACAM antibody or an antigen-binding fragment thereof, comprising a HCDR1, a HCDR2, a HCDR3, a LCDR1, a LCDR2 and a LCDR3 of SEQ ID NOs: 19, 20, 21, 22, 23, and 24, respectively;
 an isolated anti-CEACAM antibody or an antigen-binding fragment thereof, comprising a HCDR1, a HCDR2, a HCDR3, a LCDR1, a LCDR2 and a LCDR3 of SEQ ID NOs: 25, 26, 27, 28, 29, and 30, respectively;
 an isolated anti-CEACAM antibody or an antigen-binding fragment thereof, comprising a HCDR1, a HCDR2, a HCDR3, a LCDR1, a LCDR2 and a LCDR3 of SEQ ID NOs: 31, 32, 33, 34, 35, and 36, respectively; and
 an isolated anti-CEACAM antibody or an antigen-binding fragment thereof, comprising a HCDR1, a HCDR2, a HCDR3, a LCDR1, a LCDR2 and a LCDR3 of SEQ ID NOs: 37, 38, 39, 40, 41, and 42, respectively.

2. The isolated anti-CEACAM antibody or the antigen binding fragment thereof of claim 1, wherein the antibody is an IgG1, an IgG2, an IgG3 or an IgG4 isotype.

3. The isolated anti-CEACAM antibody of claim 1, wherein the antibody is a multispecific antibody.

4. The isolated anti-CEACAM antibody of claim 1, wherein the antibody is a bispecific antibody.

5. The isolated anti-CEACAM antibody or the antigen-binding fragment thereof of claim 1 conjugated to one or more heterologous molecules.

6. An isolated anti-CEACAM antibody or an antigen-binding fragment thereof, selected from the group consisting of
 an isolated anti-CEACAM antibody or an antigen-binding fragment thereof comprising a heavy chain variable region (VH) of SEQ ID NO: 79 and a light chain variable region (VL) of SEQ ID NO: 80;
 an isolated anti-CEACAM antibody or an antigen-binding fragment thereof comprising VH of SEQ ID NO: 81 and a VL of SEQ ID NO: 82;
 an isolated anti-CEACAM antibody or an antigen-binding fragment thereof comprising a VH of SEQ ID NO: 83 and a VL of SEQ ID NO: 84;
 an isolated anti-CEACAM antibody or an antigen-binding fragment thereof comprising a VH of SEQ ID NO: 85 and a VL of SEQ ID NO: 86;
 an isolated anti-CEACAM antibody or an antigen-binding fragment thereof comprising a VH of SEQ ID NO: 87 and a VL of SEQ ID NO: 88; and
 an isolated anti-CEACAM antibody or an antigen-binding fragment thereof comprising a VH of SEQ ID NO: 89 and a VL of SEQ ID NO: 90.

7. The isolated anti-CEACAM antibody or the antigen binding fragment thereof of claim 6, wherein the antibody is an IgG1, an IgG2, an IgG3 or an IgG4 isotype.

8. The isolated anti-CEACAM antibody of claim 6, wherein the antibody is a multispecific antibody.

9. The isolated anti-CEACAM antibody of claim 6, wherein the antibody is a bispecific antibody.

10. The isolated anti-CEACAM antibody or the antigen-binding fragment thereof of claim 6 conjugated to one or more heterologous molecules.

11. An isolated anti-CEACAM antibody or the antigen binding fragment thereof, wherein the antibody or the antigen binding fragment thereof competes for binding to CEACAM1, and optionally CEACAM5 or CEACAM6, with a reference antibody comprising
 a) a heavy chain variable region (VH) of SEQ ID NO: 79 and a light chain variable region (VL) of SEQ ID NO: 80; or
 b) a VH of SEQ ID NO: 81 and the VL of SEQ ID NO: 82;
 c) a VH of SEQ ID NO: 83 and the VL of SEQ ID NO: 84;
 d) a VH of SEQ ID NO: 85 and the VL of SEQ ID NO: 86;
 e) a VH of SEQ ID NO: 87 and the VL of SEQ ID NO: 88; or
 f) a VH of SEQ ID NO: 89 and the VL of SEQ ID NO: 90.

12. The isolated anti-CEACAM antibody or the antigen binding fragment thereof of claim 11, wherein the antibody is an IgG1, an IgG2, an IgG3 or an IgG4 isotype.

13. The isolated anti-CEACAM antibody of claim 11, wherein the antibody is a multispecific antibody.

14. The isolated anti-CEACAM antibody of claim 11, wherein the antibody is a bispecific antibody.

15. The isolated anti-CEACAM antibody or the antigen-binding fragment thereof of claim 11 conjugated to one or more heterologous molecules.

16. A pharmaceutical composition comprising the anti-CEACAM antibody or the antigen-binding fragment thereof selected from the group consisting of
 an isolated anti-CEACAM antibody or an antigen-binding fragment thereof, comprising a HCDR1, a HCDR2, a HCDR3, a LCDR1, a LCDR2 and a LCDR3 of SEQ ID NOs: 7, 8, 9, 10, 11, and 12, respectively;
 an isolated anti-CEACAM antibody or an antigen-binding fragment thereof, comprising a heavy chain variable region (VH) of SEQ ID NO: 79 and a light chain variable region (VL) of SEQ ID NO: 80;
 an isolated anti-CEACAM antibody or an antigen-binding fragment thereof, comprising a HCDR1, a HCDR2, a HCDR3, a LCDR1, a LCDR2 and a LCDR3 of SEQ ID NOs: 13, 14, 15, 16, 17, and 18, respectively;

an isolated anti-CEACAM antibody or an antigen-binding fragment thereof, comprising VH of SEQ ID NO: 81 and a VL of SEQ ID NO: 82;

an isolated anti-CEACAM antibody or an antigen-binding fragment thereof, comprising a HCDR1, a HCDR2, a HCDR3, a LCDR1, a LCDR2 and a LCDR3 of SEQ ID NOs: 19, 20, 21, 22, 23, and 24, respectively;

an isolated anti-CEACAM antibody or an antigen-binding fragment thereof, comprising a VH of SEQ ID NO: 83 and a VL of SEQ ID NO: 84;

an isolated anti-CEACAM antibody or an antigen-binding fragment thereof, comprising a HCDR1, a HCDR2, a HCDR3, a LCDR1, a LCDR2 and a LCDR3 of SEQ ID NOs: 25, 26, 27, 28, 29, and 30, respectively;

an isolated anti-CEACAM antibody or an antigen-binding fragment thereof, comprising a VH of SEQ ID NO: 85 and a VL of SEQ ID NO: 86;

an isolated anti-CEACAM antibody or an antigen-binding fragment thereof, comprising a HCDR1, a HCDR2, a HCDR3, a LCDR1, a LCDR2 and a LCDR3 of SEQ ID NOs: 31, 32, 33, 34, 35, and 36, respectively;

an isolated anti-CEACAM antibody or an antigen-binding fragment thereof, comprising a VH of SEQ ID NO: 87 and a VL of SEQ ID NO: 88;

an isolated anti-CEACAM antibody or an antigen-binding fragment thereof, comprising a HCDR1, a HCDR2, a HCDR3, a LCDR1, a LCDR2 and a LCDR3 of SEQ ID NOs: 37, 38, 39, 40, 41, and 42, respectively; and an isolated anti-CEACAM antibody or an antigen-binding fragment thereof of claim 11, comprising a VH of SEQ ID NO: 89 and a VL of SEQ ID NO: 90;

and a pharmaceutically acceptable carrier.

17. An isolated polynucleotide encoding the anti-CEACAM antibody or the antigen binding fragment thereof of claim 1.

18. An isolated polynucleotide encoding the anti-CEACAM antibody or the antigen binding fragment thereof of claim 6.

19. An isolated polynucleotide encoding the anti-CEACAM antibody or the antigen binding fragment thereof of claim 11.

20. An isolated polynucleotide encoding the anti-CEACAM antibody or the antigen binding fragment thereof and comprising a polynucleotide sequence encoding a sequence selected from the group consisting of SEQ ID NOs: 79-102.

21. A vector comprising the polynucleotide of claim 20.

22. A host cell comprising the vector of claim 21.

23. A method of producing the anti-CEACAM antibody or the antigen binding fragment thereof of wherein the anti-CECAM antibody or the antigen binding fragment thereof is selected from the group consisting of an isolated anti-CEACAM antibody or an antigen-binding fragment thereof, comprising a HCDR1, a HCDR2, a HCDR3, a LCDR1, a LCDR2 and a LCDR3 of SEQ ID NOs: 7, 8, 9, 10, 11, and 12, respectively;

an isolated anti-CEACAM antibody or an antigen-binding fragment thereof, comprising a heavy chain variable region (VH) of SEQ ID NO: 79 and a light chain variable region (VL) of SEQ ID NO: 80;

an isolated anti-CEACAM antibody or an antigen-binding fragment thereof, comprising a HCDR1, a HCDR2, a HCDR3, a LCDR1, a LCDR2 and a LCDR3 of SEQ ID NOs: 13, 14, 15, 16, 17, and 18, respectively;

an isolated anti-CEACAM antibody or an antigen-binding fragment thereof, comprising VH of SEQ ID NO: 81 and a VL of SEQ ID NO: 82;

an isolated anti-CEACAM antibody or an antigen-binding fragment thereof, comprising a HCDR1, a HCDR2, a HCDR3, a LCDR1, a LCDR2 and a LCDR3 of SEQ ID NOs: 19, 20, 21, 22, 23, and 24, respectively;

an isolated anti-CEACAM antibody or an antigen-binding fragment thereof, comprising a VH of SEQ ID NO: 83 and a VL of SEQ ID NO: 84;

an isolated anti-CEACAM antibody or an antigen-binding fragment thereof, comprising a HCDR1, a HCDR2, a HCDR3, a LCDR1, a LCDR2 and a LCDR3 of SEQ ID NOs: 25, 26, 27, 28, 29, and 30, respectively;

an isolated anti-CEACAM antibody or an antigen-binding fragment thereof, comprising a VH of SEQ ID NO: 85 and a VL of SEQ ID NO: 86;

an isolated anti-CEACAM antibody or an antigen-binding fragment thereof, comprising a HCDR1, a HCDR2, a HCDR3, a LCDR1, a LCDR2 and a LCDR3 of SEQ ID NOs: 31, 32, 33, 34, 35, and 36, respectively;

an isolated anti-CEACAM antibody or an antigen-binding fragment thereof, comprising a VH of SEQ ID NO: 87 and a VL of SEQ ID NO: 88;

an isolated anti-CEACAM antibody or an antigen-binding fragment thereof, comprising a HCDR1, a HCDR2, a HCDR3, a LCDR1, a LCDR2 and a LCDR3 of SEQ ID NOs: 37, 38, 39, 40, 41, and 42, respectively; and comprising culturing the host cell of claim 22 in conditions that the antibody is expressed, and recovering the antibody produced by the host cell.

\* \* \* \* \*